(12) United States Patent
Fengler et al.

(10) Patent No.: US 8,630,698 B2
(45) Date of Patent: Jan. 14, 2014

(54) FILTER FOR USE WITH IMAGING ENDOSCOPES

(75) Inventors: John J. P. Fengler, North Vancouver (CA); Francis Regamey, Vancouver (CA)

(73) Assignee: Novadaq Technologies, Inc., Mississauga, CA (US)

( * ) Notice: Subject to any disclaimer, the term of this patent is extended or adjusted under 35 U.S.C. 154(b) by 679 days.

(21) Appl. No.: 11/412,715

(22) Filed: Apr. 26, 2006

(65) Prior Publication Data

US 2007/0015963 A1 Jan. 18, 2007

Related U.S. Application Data

(63) Continuation-in-part of application No. 11/122,267, filed on May 4, 2005, now abandoned.

(51) Int. Cl.
*A61B 6/00* (2006.01)

(52) U.S. Cl.
USPC .......................................... 600/478; 600/160

(58) Field of Classification Search
USPC ................ 600/109, 158–160, 178, 309–344, 600/473–480
See application file for complete search history.

(56) References Cited

U.S. PATENT DOCUMENTS

| | | |
|---|---|---|
| 3,971,068 A | 7/1976 | Gerhardt et al. |
| 4,115,812 A | 9/1978 | Akatsu |
| 4,149,190 A | 4/1979 | Wessler et al. |
| 4,200,801 A | 4/1980 | Schuresko |
| 4,355,325 A | 10/1982 | Nakamura et al. |
| 4,378,571 A | 3/1983 | Handy |
| 4,449,535 A | 5/1984 | Renault |
| 4,532,918 A | 8/1985 | Wheeler |
| 4,556,057 A | 12/1985 | Hiruma et al. |
| 4,638,365 A | 1/1987 | Kato |
| 4,768,513 A | 9/1988 | Suzuki |
| 4,786,813 A | 11/1988 | Svanberg et al. |
| 4,821,117 A | 4/1989 | Sekiguchi |

(Continued)

FOREIGN PATENT DOCUMENTS

| | | |
|---|---|---|
| DE | 195 35 114 A1 | 3/1996 |
| DE | 196 08 027 A1 | 9/1996 |

(Continued)

OTHER PUBLICATIONS

Alfano, R.R., et al., "Fluorescence Spectra From Cancerous and Normal Human Breast and Lung Tissues," *IEEE Journal of Quantum Electronics.* QE-23(10):1806-1811, 1987.

Andersson-Engles, S., et al., "Tissue Diagnostics Using Laser Induced Fluorescence," *Ber. Bunsenges Physical Chemistry* 93:335-342, 1989.

(Continued)

*Primary Examiner* — Sanjay Cattungal
(74) *Attorney, Agent, or Firm* — Novak Druce Connolly Bove + Quigg LLP

(57) ABSTRACT

A fluorescence endoscopy video system includes a multi-mode light source that produces light for white light and fluorescence imaging modes. A filter is positioned at the distal end of an imaging endoscope so that the endoscope can produce fluorescence and white light images of a tissue sample.

20 Claims, 16 Drawing Sheets

(56) References Cited

U.S. PATENT DOCUMENTS

| | | | |
|---|---|---|---|
| 4,837,625 A | 6/1989 | Douziech et al. | |
| 4,856,495 A | 8/1989 | Tohjoh et al. | |
| 4,930,516 A | 6/1990 | Alfano et al. | |
| 4,951,135 A | 8/1990 | Sasagawa et al. | |
| 4,954,897 A | 9/1990 | Ejima et al. | |
| 4,974,936 A | 12/1990 | Ams et al. | |
| 5,001,556 A | 3/1991 | Nakamura et al. | |
| 5,007,408 A | 4/1991 | Ieoka | |
| 5,034,888 A | 7/1991 | Uehara et al. | |
| 5,134,662 A | 7/1992 | Bacus et al. | |
| 5,165,079 A | 11/1992 | Schulz-Hennig | |
| 5,214,503 A | 5/1993 | Chiu et al. | |
| 5,225,883 A | 7/1993 | Carter et al. | |
| 5,255,087 A | 10/1993 | Nakamura et al. | |
| 5,278,642 A | 1/1994 | Danna et al. | |
| 5,365,057 A | 11/1994 | Morley et al. | |
| 5,371,355 A | 12/1994 | Wodecki | |
| 5,377,686 A | 1/1995 | O'Rourke et al. | |
| 5,408,263 A | 4/1995 | Kikuchi et al. | |
| 5,410,363 A | 4/1995 | Capen et al. | |
| 5,419,323 A | 5/1995 | Kittrell et al. | |
| 5,420,628 A | 5/1995 | Poulsen et al. | |
| 5,421,337 A * | 6/1995 | Richards-Kortum et al. | 600/477 |
| 5,424,841 A | 6/1995 | Van Gelder et al. | |
| 5,430,476 A | 7/1995 | Häfele et al. | |
| 5,485,203 A | 1/1996 | Nakamura et al. | |
| 5,507,287 A | 4/1996 | Palcic et al. | |
| 5,536,236 A * | 7/1996 | Yabe et al. | 600/125 |
| 5,585,846 A | 12/1996 | Kim | |
| 5,590,660 A * | 1/1997 | MacAulay et al. | 600/478 |
| 5,596,654 A | 1/1997 | Tanaka | |
| 5,646,680 A | 7/1997 | Yajima | |
| 5,647,368 A | 7/1997 | Zeng et al. | |
| 5,697,373 A * | 12/1997 | Richards-Kortum et al. | 600/475 |
| 5,749,830 A | 5/1998 | Kaneko et al. | |
| 5,772,580 A | 6/1998 | Utsui et al. | |
| 5,827,190 A | 10/1998 | Palcic et al. | |
| 5,852,498 A | 12/1998 | Youvan et al. | |
| 5,891,016 A | 4/1999 | Utsui et al. | |
| 5,971,918 A | 10/1999 | Zanger | |
| 5,984,861 A | 11/1999 | Crowley | |
| 5,986,271 A | 11/1999 | Lazarev et al. | |
| 5,990,996 A * | 11/1999 | Sharp | 349/119 |
| 5,999,240 A * | 12/1999 | Sharp et al. | 349/119 |
| 6,002,137 A | 12/1999 | Hayashi | |
| 6,008,889 A | 12/1999 | Zeng et al. | |
| 6,021,344 A | 2/2000 | Lui et al. | |
| 6,028,622 A | 2/2000 | Suzuki | |
| 6,059,720 A | 5/2000 | Furusawa et al. | |
| 6,061,591 A | 5/2000 | Freitag et al. | |
| 6,069,689 A | 5/2000 | Zeng et al. | |
| 6,070,096 A | 5/2000 | Hayashi | |
| 6,095,982 A * | 8/2000 | Richards-Kortum et al. | 600/476 |
| 6,099,466 A | 8/2000 | Sano et al. | |
| 6,110,106 A * | 8/2000 | MacKinnon et al. | 600/181 |
| 6,120,435 A | 9/2000 | Eino | |
| 6,148,227 A | 11/2000 | Wagnières et al. | |
| 6,161,035 A | 12/2000 | Furusawa | |
| 6,192,267 B1 | 2/2001 | Scherninski et al. | |
| 6,212,425 B1 | 4/2001 | Irion et al. | |
| 6,258,576 B1 * | 7/2001 | Richards-Kortum et al. | 435/40.52 |
| 6,280,378 B1 | 8/2001 | Kazuhiro et al. | |
| 6,293,911 B1 | 9/2001 | Imaizumi et al. | |
| 6,364,829 B1 | 4/2002 | Fulghum | |
| 6,364,831 B1 | 4/2002 | Crowley | |
| 6,422,994 B1 | 7/2002 | Kaneko et al. | |
| 6,526,213 B1 * | 2/2003 | Ilenda et al. | 385/143 |
| 6,529,768 B1 | 3/2003 | Hakamata | |
| 6,537,211 B1 * | 3/2003 | Wang et al. | 600/178 |
| 6,603,552 B1 | 8/2003 | Cline et al. | |
| 6,639,664 B2 * | 10/2003 | Haan et al. | 356/241.1 |
| 6,772,003 B2 * | 8/2004 | Kaneko et al. | 600/476 |
| 6,786,865 B2 * | 9/2004 | Dhindsa | 600/159 |
| 6,899,675 B2 * | 5/2005 | Cline et al. | 600/160 |
| 7,235,045 B2 * | 6/2007 | Wang et al. | 600/109 |
| 7,236,815 B2 * | 6/2007 | Richards-Kortum et al. | 600/407 |
| 7,341,557 B2 * | 3/2008 | Cline et al. | 600/160 |
| 7,722,534 B2 * | 5/2010 | Cline et al. | 600/160 |
| 7,798,955 B2 * | 9/2010 | Ishihara et al. | 600/101 |
| 2002/0035330 A1 * | 3/2002 | Cline et al. | 600/476 |
| 2002/0138008 A1 | 9/2002 | Tsujita et al. | |
| 2002/0161283 A1 | 10/2002 | Sendai | |
| 2002/0175993 A1 * | 11/2002 | Ueno et al. | 348/68 |
| 2002/0177778 A1 * | 11/2002 | Averback et al. | 600/476 |
| 2003/0002036 A1 * | 1/2003 | Haan et al. | 356/241.1 |
| 2003/0042493 A1 * | 3/2003 | Kazakevich | 257/98 |
| 2003/0135092 A1 * | 7/2003 | Cline et al. | 600/160 |
| 2003/0153811 A1 | 8/2003 | Muckner | |
| 2004/0010183 A1 * | 1/2004 | Dhindsa | 600/159 |
| 2006/0089554 A1 * | 4/2006 | Ishihara et al. | 600/476 |
| 2006/0211915 A1 | 9/2006 | Takeuchi et al. | |
| 2006/0217594 A1 | 9/2006 | Ferguson | |
| 2008/0021274 A1 * | 1/2008 | Bayer et al. | 600/112 |

FOREIGN PATENT DOCUMENTS

| | | |
|---|---|---|
| EP | 0 512 965 A1 | 11/1992 |
| EP | 0 774 685 A2 | 5/1997 |
| EP | 0 792 618 A1 | 9/1997 |
| FR | 2 671 405 | 7/1992 |
| JP | 60-246733 A | 12/1985 |
| JP | 61-159936 A | 7/1986 |
| JP | 3-97439 A | 4/1991 |
| JP | 3-97441 A | 4/1991 |
| JP | 3-97442 A | 4/1991 |
| JP | 6-125911 A | 5/1994 |
| JP | 07-155285 | 6/1995 |
| JP | 07-155286 | 6/1995 |
| JP | 07-155290 | 6/1995 |
| JP | 07-155291 | 6/1995 |
| JP | 07-155292 | 6/1995 |
| JP | 07-204156 A | 8/1995 |
| JP | 07-222712 | 8/1995 |
| JP | 07-250804 | 10/1995 |
| JP | 07-250812 | 10/1995 |
| JP | 08-140928 A | 6/1996 |
| JP | 08-140929 A | 6/1996 |
| JP | 08-224208 A | 9/1996 |
| JP | 08-224209 | 9/1996 |
| JP | 08-224210 A | 9/1996 |
| JP | 08-224240 | 9/1996 |
| JP | 08-252218 | 10/1996 |
| JP | 09-066023 A | 3/1997 |
| JP | 09-070384 A | 3/1997 |
| JP | 10-127563 | 5/1998 |
| JP | 10-151104 A | 6/1998 |
| JP | 10-201700 A | 8/1998 |
| JP | 10-201707 A | 8/1998 |
| JP | 10-225426 | 8/1998 |
| JP | 10-225427 A | 8/1998 |
| JP | 10-243915 | 9/1998 |
| JP | 10-243920 | 9/1998 |
| JP | 10-308114 | 11/1998 |
| JP | 10-309281 | 11/1998 |
| JP | 10-309282 | 11/1998 |
| JP | 10-328129 | 12/1998 |
| JP | 11-089789 | 4/1999 |
| JP | 11-104059 | 4/1999 |
| JP | 11-104060 | 4/1999 |
| JP | 11-104061 | 4/1999 |
| JP | 11-104070 A | 4/1999 |
| JP | 11-113839 | 4/1999 |
| JP | 11-155812 | 6/1999 |
| JP | 11-332819 | 12/1999 |
| JP | 2000-354583 A | 12/2000 |
| JP | 2005058618 A2 | 3/2005 |
| JP | 2005058619 A2 | 3/2005 |
| JP | 2005058620 A2 | 3/2005 |
| JP | 2005080819 A2 | 3/2005 |
| JP | 2005081079 A2 | 3/2005 |
| WO | WO 95/26673 | 10/1995 |

(56) References Cited

FOREIGN PATENT DOCUMENTS

| | | |
|---|---|---|
| WO | WO 98/24360 | 6/1998 |
| WO | WO 99/01749 A1 | 1/1999 |
| WO | WO 99/53832 A1 | 10/1999 |
| WO | WO 00/42910 | 7/2000 |
| WO | WO 00/54652 A1 | 9/2000 |

OTHER PUBLICATIONS

Bhunchet, E., et al. "Fluorescein Electronic Endoscopy: A Novel Method for Detection of Early Stage Gastric Cancer Not Evident to Routine Endoscopy," *Gastrointesinal Endoscopy* 55(4):562-571, 2002.

Hung, J., et al., "Autofluorescence of Normal and Malignant Bronchial Tissue," *Lasers in Surgery and Medicine* 11:99-105, 1991.

\* cited by examiner

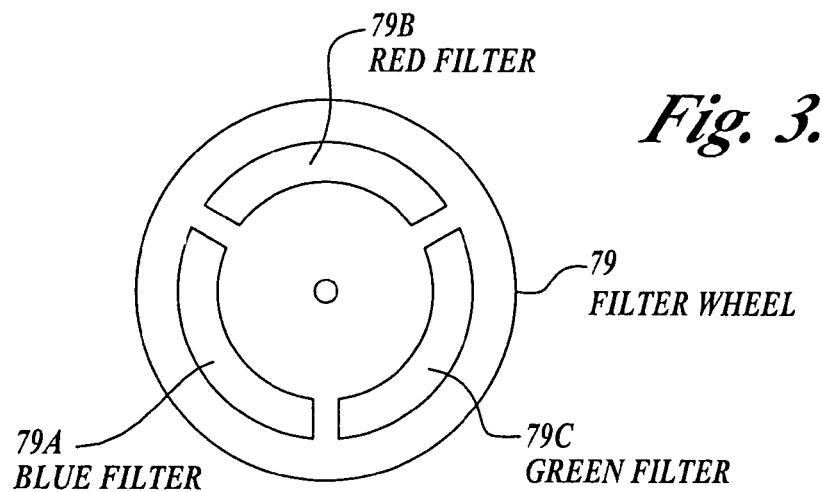
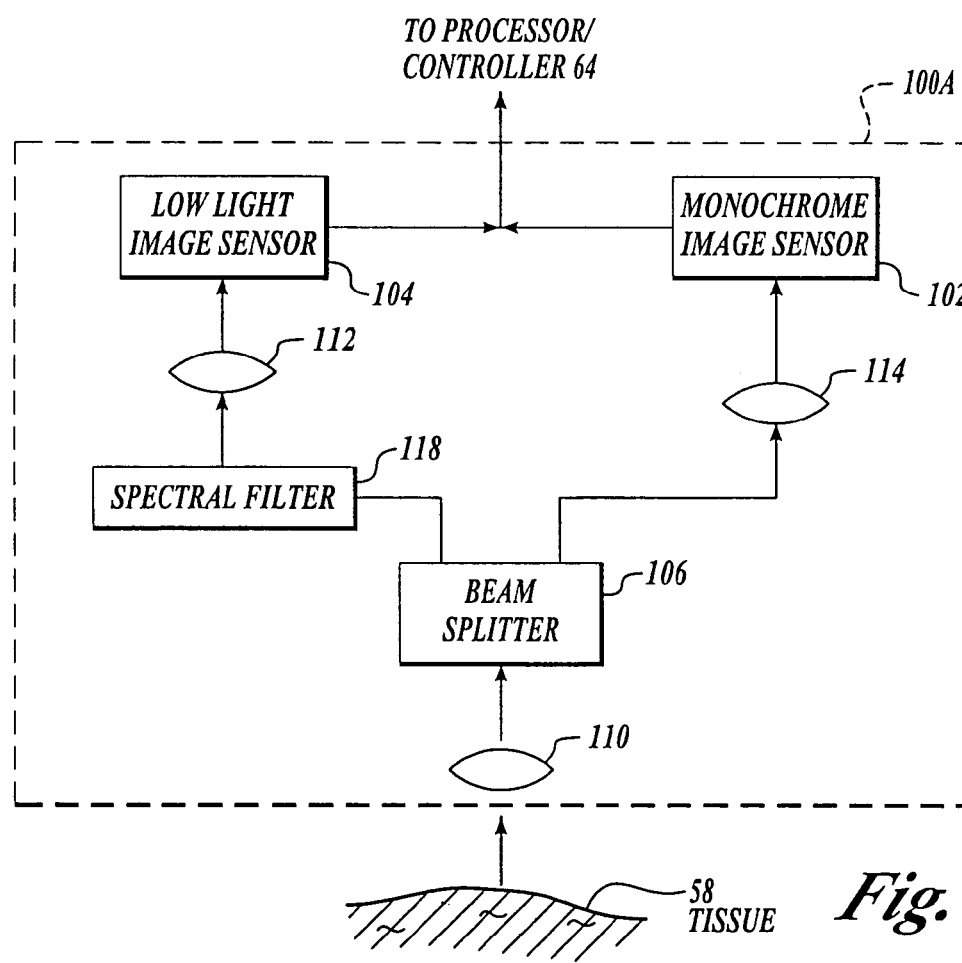

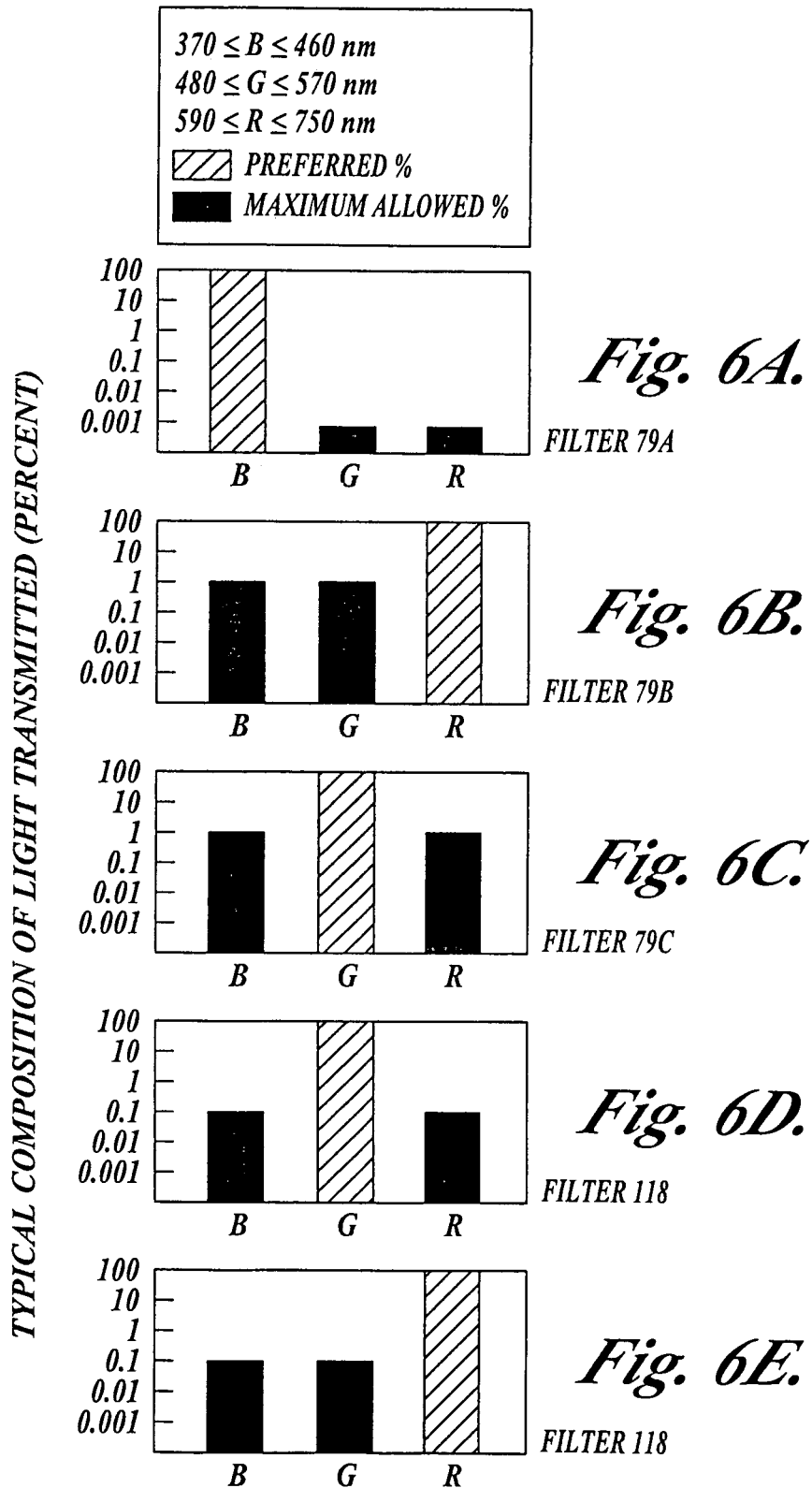

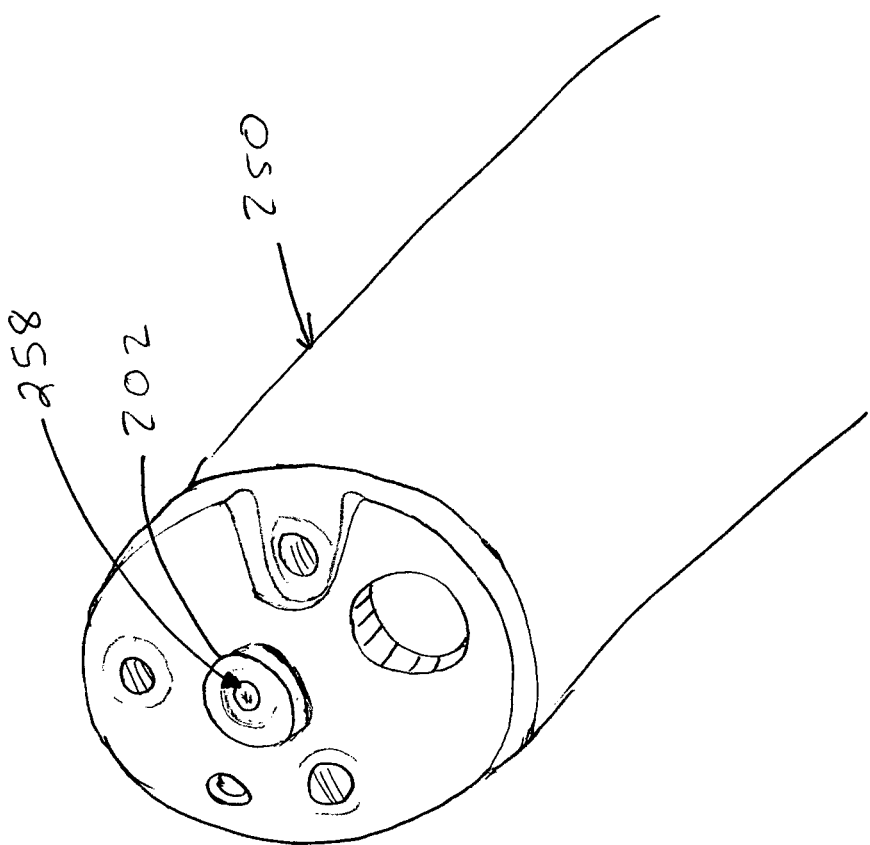

FILTER FOR USE WITH IMAGING ENDOSCOPES

CROSS-REFERENCES TO RELATED APPLICATIONS

This application is a continuation-in-part of U.S. patent application Ser. No. 11/122,267, filed May 4, 2005, the benefit of the filing date of which is being claimed under 35 U.S.C. §120.

FIELD OF THE INVENTION

The present invention relates to medical imaging systems in general, and in particular to fluorescence endoscopy video systems.

BACKGROUND OF THE INVENTION

Fluorescence endoscopy utilizes differences in the fluorescence response of normal tissue and tissue suspicious for early cancer as a tool in the detection and localization of such cancer. The fluorescing compounds or fluorophores that are excited during fluorescence endoscopy may be exogenously applied photo-active drugs that accumulate preferentially in suspicious tissues, or they may be the endogenous fluorophores that are present in all tissue. In the latter case, the fluorescence from the tissue is typically referred to as autofluorescence or native fluorescence. Tissue autofluorescence is typically due to fluorophores with absorption bands in the UV and blue portion of the visible spectrum and emission bands in the green to red portions of the visible spectrum. In tissue suspicious for early cancer, the green portion of the autofluorescence spectrum is significantly suppressed. Fluorescence endoscopy that is based on tissue autofluorescence utilizes this spectral difference to distinguish normal from suspicious tissue.

Since the concentration and/or quantum efficiency of the endogenous fluorophores in tissue is relatively low, the fluorescence emitted by these fluorophores is not typically visible to the naked eye. Fluorescence endoscopy is consequently performed by employing low light image sensors to acquire images of the fluorescing tissue through the endoscope. The images acquired by these sensors are most often encoded as video signals and displayed on a color video monitor. Representative fluorescence endoscopy video systems that image tissue autofluorescence are disclosed in U.S. Pat. No. 5,507,287, issued to Palcic et al.; U.S. Pat. No. 5,590,660, issued to MacAulay et al.; U.S. Pat. No. 5,827,190, issued to Palcic et al., U.S. patent application Ser. No. 09/615,965, and U.S. patent application Ser. No. 09/905,642, all of which are herein incorporated by reference. Each of these is assigned to Xillix Technologies Corp. of Richmond, British Columbia, Canada, the assignee of the present application.

While the systems disclosed in the above-referenced patents are significant advances in the field of early cancer detection, improvements can be made. In particular, it is desirable to reduce the size, cost, weight, and complexity of the camera.

SUMMARY OF THE INVENTION

A fluorescence endoscopy video system in accordance with one aspect of the present invention includes an endoscopic light source that is capable of operating in multiple modes to produce either white light, reflectance light, fluorescence excitation light, or fluorescence excitation light with reference reflectance light. An endoscope incorporates a light guide for transmitting light to the tissue under observation and includes either an imaging guide or a compact camera disposed in the insertion portion of the endoscope for receiving light from the tissue under observation. A compact camera includes at least one low light imaging sensor that receives light from the tissue and is capable of operating in multiple imaging modes to acquire color or multi-channel fluorescence and reflectance images. The system further includes an image processor and system controller that digitizes, processes and encodes the image signals produced by the image sensor(s) as a color video signal and a color video monitor that displays the processed video images.

In accordance with another embodiment of the invention, a filter is placed at the distal end of a conventional endoscope in order to produce both autofluorescence and white light images from an image sensor. The filter blocks excitation light from reaching an image sensor, but passes some blue light so that both fluorescence images and color/white light images of tissue can be produced. In one embodiment of the invention, a light source that produces excitation light, also produces a color corrected illumination light such that color images of the tissue can be white balanced.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 shows a filter wheel and optical filters for the multi-mode light source;

FIGS. 4A-4C illustrate a number of alternative embodiments of a camera that can acquire color and/or fluorescence/reflectance images according to one aspect of the present invention with optional placement for collimation and imaging optics;

FIGS. 6A-6E are graphs illustrating transmission characteristics of filters utilized for color imaging and fluorescence/reflectance imaging with the camera embodiments shown in FIGS. 4A-4C;

FIG. 12 illustrates another embodiment of a distal end filter that is secured to an endoscope in accordance with the present invention.

DETAILED DESCRIPTION

Figure 1A:
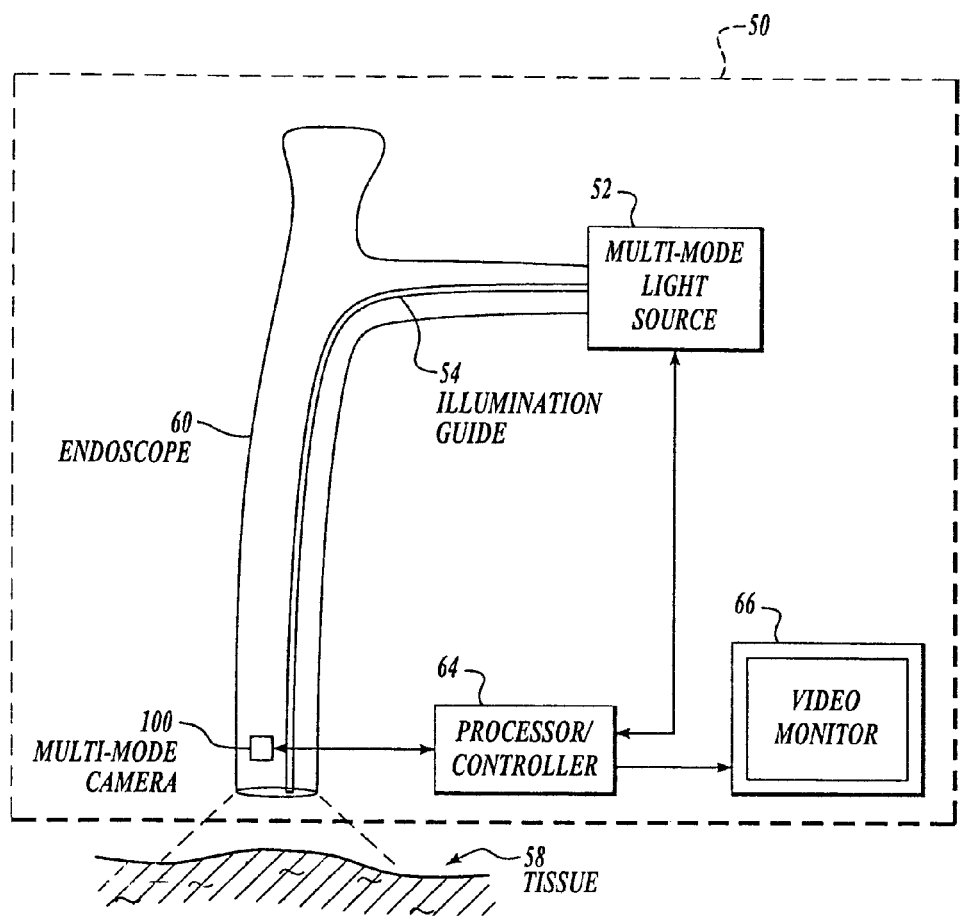
FIG. 1A-1B are block diagrams of a fluorescence endoscopy video system according to two embodiments of the present invention.

FIG. 1A is a block diagram of a fluorescence endoscopy video system 50 in accordance with one embodiment of the present invention. The system includes a multi-mode light source 52 that generates light for obtaining color and fluorescence images. The use of the light source for obtaining different kinds of images will be described in further detail below. Light from the light source 52 is supplied to an illumination guide 54 of an endoscope 60, which then illuminates a tissue sample 58 that is to be imaged.

As shown in FIG. 1A, the system also includes a multi-mode camera 100, which is located at the insertion end of the endoscope 60. The light from the tissue is directly captured by the multi-mode camera 100. With the multi-mode camera 100 located at the insertion end of the endoscope, the resulting endoscope 60 can be characterized as a fluorescence video endoscope, similar to video endoscopes currently on the market (such as the Olympus CF-Q180AL/I or CF-240L) in utility, but with the ability to be utilized for fluorescence/reflectance and/or fluorescence/fluorescence imaging, in additional to conventional color imaging. Fluorescence/reflectance and fluorescence/fluorescence imaging will be described in detail below. By locating the camera at the insertion end of the endoscope, the inherent advantages of a video endoscope can be obtained; namely, the light available to form an image and the image resolution are improved compared to the case when the image is transmitted outside the body through an endoscope imaging guide or relay lens system.

A processor/controller 64 controls the multi-mode camera 100 and the light source 52, and produces video signals that are displayed on a video monitor 66. The processor/controller 64 communicates with the multi-mode camera 100 with wires or other signal carrying devices that are routed within the endoscope. Alternatively, communication between the processor/controller 64 and the camera 100 can be conducted over a wireless link.

Figure 1B:
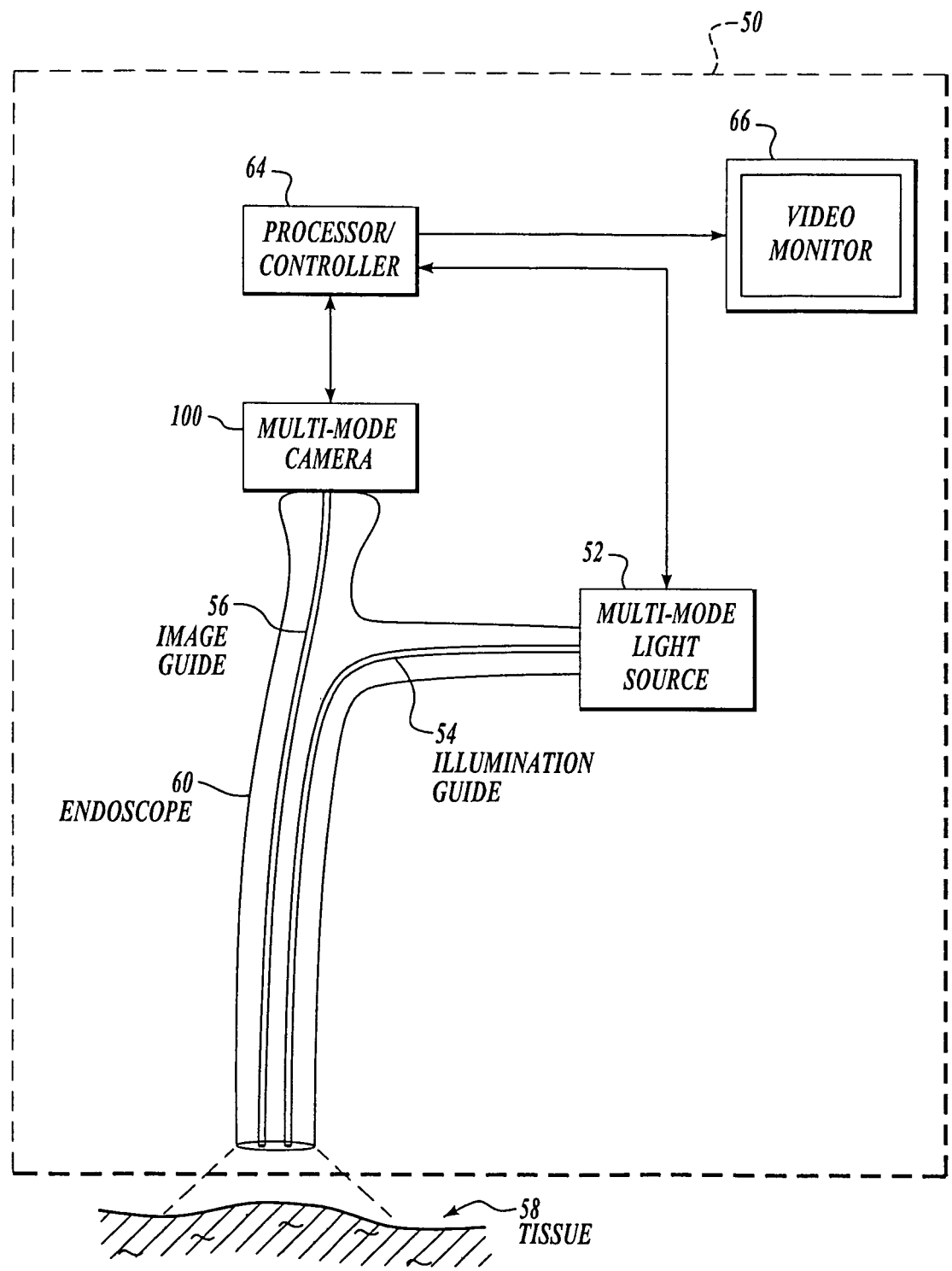

FIG. 1B is a block diagram of an alternative fluorescence endoscopy video system 50, which differs from that shown in FIG. 1A in that endoscope 60 also incorporates an image guide 56 and the multi-mode camera 100 is attached to an external portion of the endoscope that is outside the body. The light that is collected from the tissue by endoscope 60 is transmitted through the image guide 56 and projected into the multi-mode camera 100. Other than the addition of the image guide 56 to endoscope 100 and the location of the multi-mode camera 100 at the external end of the endoscope, the system of FIG. 1B is identical to that shown in FIG. 1A.

Figure 2A:
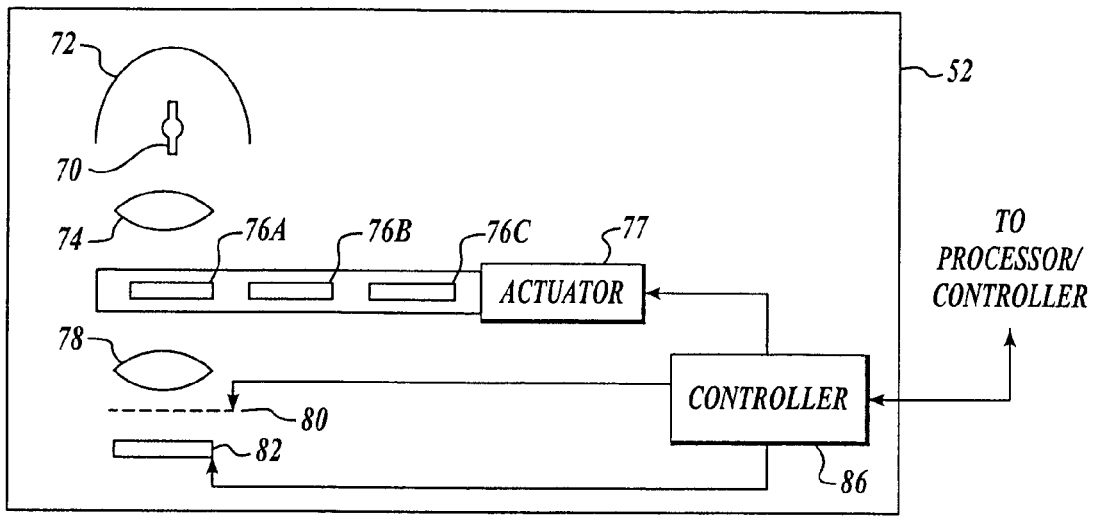
FIGS. 2A-2B are block diagrams of a multi-mode light source in accordance with different embodiments of the present invention.

FIG. 2A shows the components of the light source 52 in greater detail. The light source 52 includes an arc lamp 70 that is surrounded by a reflector 72. In one embodiment of the invention, the arc lamp 70 is a high pressure mercury arc lamp (such as the Osram VIP R 150/P24 or HXP R 200W/45). Alternatively, other arc lamps, solid state devices (such as light emitting diodes or diode lasers), or broadband light sources may be used, but a high pressure mercury lamp is currently preferred for its combination of high blue light output and small arc size.

The light from the arc lamp 70 is coupled to a light guide 54 of the endoscope 60 through appropriate optics 74, 76, and 78 for light collection, spectral filtering and focusing respectively. The light from the arc lamp is spectrally filtered by one of a number of optical filters 76A, 76B, 76C ... that operate to pass or reject desired wavelengths of light in accordance with the operating mode of the system. As used herein, "wavelength" is to be interpreted broadly to include not only a single wavelength, but a range of wavelengths as well.

An intensity control 80 that adjusts the amount of light transmitted along the light path is positioned at an appropriate location between the arc lamp 70 and the endoscope light guide 54. In addition, a shutter mechanism 82 may be positioned in the same optical path in order to block any of the light from the lamp from reaching the light guide. A controller 86 operates an actuator 77 that moves the filters 76A, 76B or 76C into and out of the light path. The controller 86 also controls the position of the intensity control 80 and may control the operation of the shutter mechanism 82.

The transmission characteristics of filters 76A, 76B, 76C, ..., the characteristics of the actuator 77 mechanism, and the time available for motion of the filters 76A, 76B, 76C, ..., into and out of the light path, depend on the mode of operation required for use with the various camera embodiments. The requirements fall into two classes. If the light source shown in FIG. 2A is of the class wherein only one filter is utilized per imaging mode, the appropriate filter is moved in or out of the light path only when the imaging mode is changed. In that case, the actuator 77 only need change the filter in a time of approximately 1.0 second. The optical filter characteristics of filters 76A, 76B ... are tailored for each imaging mode. For example, optical filter 76A, used for color imaging, reduces any spectral peaks and modifies the color temperature of the arc lamp 70 so that the output spectrum simulates sunlight. Optical filter 76B transmits only fluorescence excitation light for use with the fluorescence/fluorescence imaging mode and optical filter 76C transmits both fluorescence excitation light and reference reflectance light for use with the fluorescence/reflectance imaging mode.

Figure 2B:
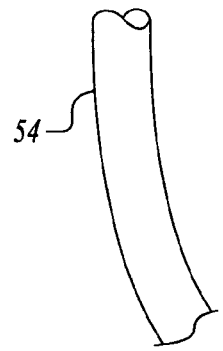

A light source 52A of a second class is illustrated in FIG. 2B; only the differences from the light source shown in FIG. 2A will be elucidated. The light source 52A uses multiple filters during each imaging mode. For example, light source filters, which provide red, green, and blue illumination sequentially for periods corresponding to a video frame or field, can be used for the acquisition of a color or a multi-spectral image with a monochrome image sensor, with the different wavelength components of the image each acquired at slightly different times. Such rapid filter changing requires a considerably different actuator than necessitated for the light source 52 of FIG. 2A. As shown in FIG. 2B, the filters are mounted on a filter wheel 79 that is rotated by a motor, which is synchronized to the video field or frame rate. The layout of the blue, red and green filters, 79A, 79B, and 79C, respectively, in filter wheel 79 are shown in FIG. 3.

The transmission characteristics of light source filters, the characteristics of the filter actuator mechanism, and the time available for motion of the filters into and out of the light path, for the two different classes of light sources are described in more detail below in the context of the various camera embodiments.

Because fluorescence endoscopy is generally used in conjunction with white light endoscopy, each of the various embodiments of the multi-mode camera 100 described below may be used both for color (white light) and fluorescence/reflectance and/or fluorescence/fluorescence imaging. (For the purposes of the present invention the terms white light imaging and color imaging of tissue are considered to be synonymous.) These camera embodiments particularly lend themselves to incorporation within a fluorescence video endoscope due to their compactness and their ability to be implemented with no moving parts.

In a first embodiment, shown in FIG. 4A, a camera 100A receives light from the tissue 58, either directly from the tissue in the case of a camera located at the insertion end of an endoscope, as shown in FIG. 1A, or by virtue of an endoscope image guide 56, which transmits the light from the tissue to the camera, as shown in FIG. 11B. The light is directed towards a monochrome image sensor 102 and a low light image sensor 104 by a fixed optical beamsplitter 106 that splits the incoming light into two beams. The light beam is split such that a smaller proportion of the light received from the tissue 58 is directed towards the monochrome image sensor 102 and a larger proportion of the incoming light is directed towards the low light image sensor 104. In this embodiment, the beamsplitter may be a standard commercially available single plate 88, single cube 89, or single pellicle design 90, as shown in FIGS. 5A-5C. It should be noted that, if the optical path between the tissue 58 and the image sensors contains an uneven number of reflections (e.g., such as from a single component beamsplitter), the image projected onto the sensor will be left-to-right inverted. The orientation of such images will need to be corrected by image processing.

In FIG. 4A, light collimating optics 110 are positioned in front of the beamsplitter 106, and imaging optics 112 and 114 are positioned immediately preceding the monochrome image sensor 102 and the low light image sensor 104, respectively. A spectral filter 118 is located in the optical path between the beamsplitter 106 and the low light image sensor 104. Alternatively, the spectral filter 118 may be incorporated as an element of the beamsplitter 106.

Figure 4B:
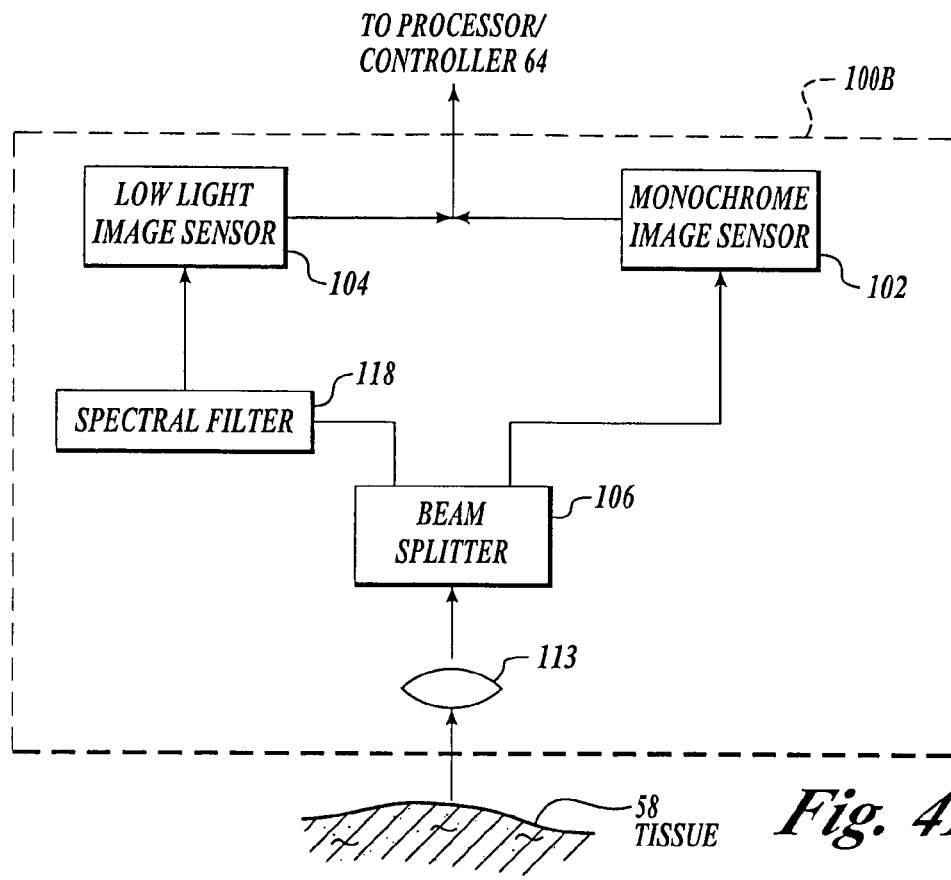
Figure 5A:
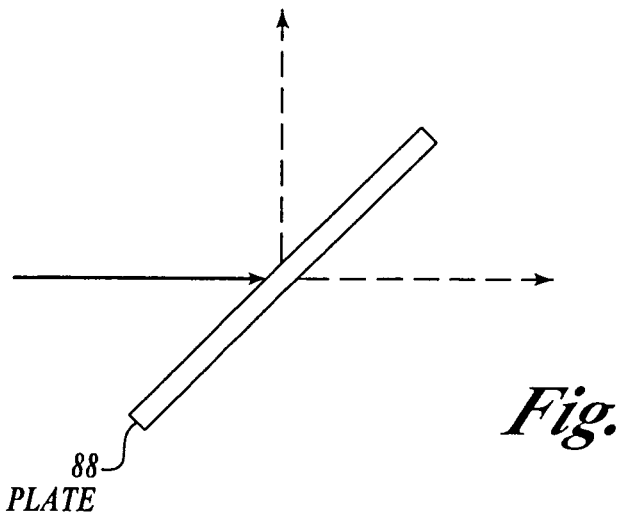
FIGS. 5A-5C illustrate a number of camera beamsplitter configurations.
Figure 5B:
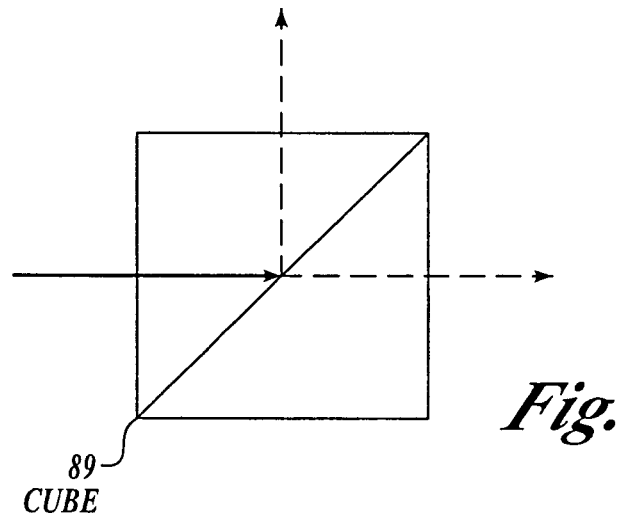
Figure 5C:
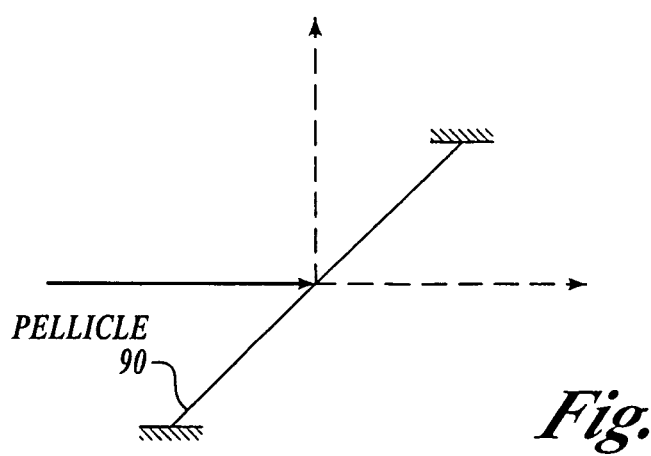

FIG. 4B illustrates another embodiment of the camera 100. A camera 100B is the same as the camera 100A described above except that the light collimating optics 110 and imaging optics 112 and 114 have been eliminated and replaced with a single set of imaging optics 113 located between the tissue and beamsplitter 106. The advantage of this configuration is that all imaging is performed and controlled by the same imaging optics 113. Such a configuration requires all beam paths to have the same optical path length, however, and this restriction must be considered in the design of the beamsplitter 106 and spectral filter 118 that is located in the path to the low light image sensor 104. In addition, the fact that these optical elements are located in a converging beam path must be considered in specifying these elements and in the design of the imaging optics 113.

The low light image sensor 104 preferably comprises a charge coupled device with charge carrier multiplication (of the same type as the Texas Instruments TC253 or the Marconi Technologies CCD65), electron beam charge coupled device (EBCCD), intensified charge coupled device (ICCD), charge injection device (CID), charge modulation device (CMD), complementary metal oxide semiconductor image sensor (CMOS) or charge coupled device (CCD) type sensor. The monochrome image sensor 102 is preferably a CCD or a CMOS image sensor.

Figure 4C:
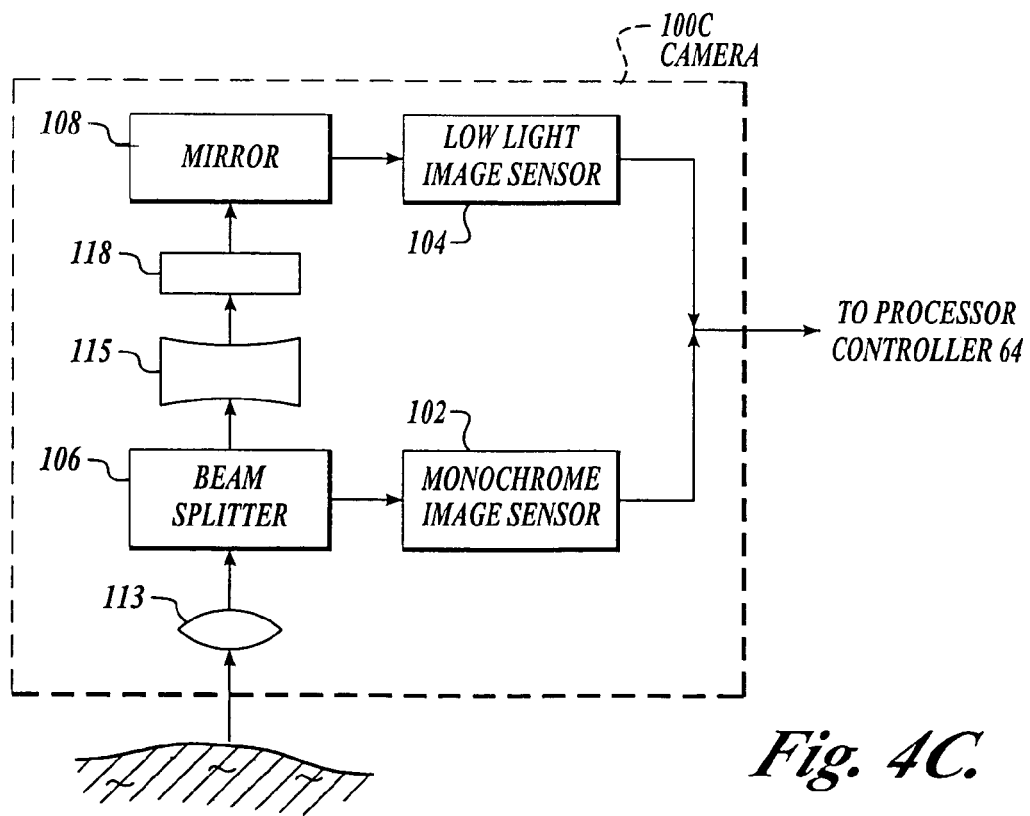

An alternative configuration of the camera 100B is shown in FIG. 4C. All aspects of this embodiment of this camera 100C are similar to the camera 100B shown in FIG. 4B except for differences which arise from reducing the width of the camera by mounting both image sensors 102 and 104 perpendicular to the camera front surface. In this alternative configuration, the low light image sensor 104 and the monochrome image sensor 102 are mounted with their image planes perpendicular to the input image plane of the camera. Light received from the tissue 58 is projected by imaging optics 113 through beamsplitter 106 onto the image sensors 102 and 104. The beamsplitter 106 directs a portion of the incoming light in one beam towards one of the sensors 102, 104. Another portion of the incoming light in a second light beam passes straight through the beamsplitter 106 and is directed by a mirror 108 towards the other of the sensors 102, 104. In addition, a second set of imaging optics 115 is utilized to account for the longer optical path to this second sensor. The images projected onto both sensors will be left-to-right inverted and should be inverted by image processing.

The processor/controller 64 as shown in FIGS. 1A and 1B receives the transduced image signals from the camera 100 and digitizes and processes these signals. The processed signals are then encoded in a video format and displayed on a color video monitor 66.

Based on operator input, the processor/controller 64 also provides control functions for the fluorescence endoscopy video system. These control functions include providing control signals that control the camera gain in all imaging modes, coordinating the imaging modes of the camera and light source, and providing a light level control signal for the light source.

The reason that two separate images in different wavelength bands are acquired in fluorescence imaging modes of the fluorescence endoscopy video systems described herein, and the nature of the fluorescence/reflectance and fluorescence/fluorescence imaging, will now be explained. It is known that the intensity of the autofluorescence at certain wavelengths changes as tissues become increasingly abnormal (i.e., as they progress from normal to frank cancer). When visualizing images formed from such a band of wavelengths of autofluorescence, however, it is not easy to distinguish between those changes in the signal strength that are due to pathology and those that are due to imaging geometry and shadows. A second fluorescence image acquired in a band of wavelengths in which the image signal is not significantly affected by tissue pathology, utilized for fluorescence/fluorescence imaging, or a reflected light image acquired in a band of wavelengths in which the image signal is not significantly affected by tissue pathology consisting of light that has undergone scattering within the tissue (known as diffuse reflectance), utilized for fluorescence/reflectance imaging, may be used as a reference signal with which the signal strength of the first fluorescence image can be "normalized." Such normalization is described in two patents previously incorporated herein by reference: U.S. Pat. No. 5,507,287, issued to Palcic et al., describes fluorescence/fluorescence imaging and U.S. Pat. No. 5,590,660, issued to MacAulay et al., describes fluorescence/reflectance imaging.

One technique for performing the normalization is to assign each of the two image signals a different display color, e.g., by supplying the image signals to different color inputs of a color video monitor. When displayed on a color video monitor, the two images are effectively combined to form a single image, the combined color of which represents the relative strengths of the signals from the two images. Since light originating from fluorescence within tissue and diffuse reflectance light which has undergone scattering within the tissue are both emitted from the tissue with a similar spatial distribution of intensities, the color of a combined image is independent of the absolute strength of the separate image signals, and will not change as a result of changes in the distance or angle of the endoscope 60 to the tissue sample 58, or changes in other imaging geometry factors. If, however, there is a change in the shape of the autofluorescence spectrum of the observed tissue that gives rise to a change in the relative strength of the two image signals, such a change will be represented as a change in the color of the displayed image. Another technique for performing the normalization is to calculate the ratio of the pixel intensities at each location in the two images. A new image can then be created wherein each pixel has an intensity and color related to the ratio computed. The new image can then be displayed by supplying it to a color video monitor.

The mixture of colors with which normal tissue and tissue suspicious for early cancer are displayed depends on the gain applied to each of the two separate image signals. There is an optimal gain ratio for which tissue suspicious for early cancer in a fluorescence image will appear as a distinctly different color than normal tissue. This gain ratio is said to provide the operator with the best combination of sensitivity (ability to detect suspect tissue) and specificity (ability to discriminate correctly). If the gain applied to the reference image signal is too high compared to the gain applied to the fluorescence image signal, the number of tissue areas that appear suspicious, but whose pathology turns out to be normal, increases. Conversely, if the relative gain applied to the reference image signal is too low, sensitivity decreases and suspect tissue will appear like normal tissue. For optimal system performance, therefore, the ratio of the gains applied to the image signals must be maintained at all times. The control of the gain ratio is described in two patent applications previously incorporated herein by reference: U.S. patent application Ser. No. 09/615,965, and U.S. patent application Ser. No. 09/905,642.

In vivo spectroscopy has been used to determine which differences in tissue autofluorescence and reflectance spectra have a pathological basis. The properties of these spectra determine the particular wavelength bands of autofluorescence and reflected light required for the fluorescence/reflectance imaging mode, or the particular two wavelength bands of autofluorescence required for fluorescence/fluorescence imaging mode. Since the properties of the spectra depend on the tissue type, the wavelengths of the important autofluorescence band(s) may depend on the type of tissue being imaged. The specifications of the optical filters described below are a consequence of these spectral characteristics, and are chosen to be optimal for the tissues to be imaged.

As indicated above, the filters in the light source and camera should be optimized for the imaging mode of the camera, the type of tissue to be examined and/or the type of precancerous tissue to be detected. Although all of the filters described below can be made to order using standard, commercially available components, the appropriate wavelength range of transmission and degree of blocking outside of the desired transmission range for the described fluorescence endoscopy images are important to the proper operation of the system. The importance of other issues in the specification of such filters, such as the fluorescence properties of the filter materials and the proper use of anti-reflection coatings, are taken to be understood.

FIGS. 6A-6E illustrate the preferred filter characteristics for use in a fluorescence endoscopy system having a camera of the type shown in FIGS. 4A-4C and light source as shown in FIG. 2B, that operates in a fluorescence/reflectance imaging mode, or a color imaging mode. There are several possible configurations of fluorescence endoscopy video systems, operating in the fluorescence/reflectance imaging mode including green fluorescence with either red or blue reflectance, and red fluorescence with either green or blue reflectance. The particular configuration utilized depends on the target clinical organ and application. The filter characteristics will now be described for each of these four configurations.

FIG. 6A illustrates the composition of the light transmitted by a blue filter, such as filter 79A, which is used to produce excitation light in the system light source. This filter transmits light in the wavelength range from 370-460 nm or any subset of wavelengths in this range. Of the light transmitted by this filter, less than 0.001% is in the fluorescence imaging band from 480-750 nm (or whatever desired subsets of this range is within the specified transmission range of the primary and reference fluorescence image filters described below).

FIG. 6B illustrates the composition of the light transmitted by a red filter, such as filter 79B, which is used to produce red reflectance light in the system light source. This filter transmits light in the wavelength range from 590-750 nm or any subset of wavelengths in this range. Light transmitted outside this range should not exceed 1%.

FIG. 6C illustrates the composition of the light transmitted by a green filter, such as filter 79C, which is used to produce green reflectance light in the system light source. This filter transmits light in the wavelength range from 480-570 nm or any subset of wavelengths in this range. Light transmitted outside this range should not exceed 1%.

FIG. 6D shows the composition of the light transmitted by a camera spectral filter, such as filter 118, for defining the primary fluorescence image in the green spectral band. In this configuration, the filter blocks excitation light and red fluorescence light while transmitting green fluorescence light in the wavelength range of 480-570 nm or any subset of wavelengths in this range. When used in a fluorescence endoscopy video system with the light source filter 79A described above, the filter characteristics are such that any light outside of the wavelength range of 480-570 nm, or any desired subset of wavelengths in this range, contributes no more than 0.1% to the light transmitted by the filter.

FIG. 6E shows the composition of the light transmitted by a camera filter, such as filter 118, for defining the primary fluorescence image in the red spectral band. In this configuration, the filter blocks excitation light and green fluorescence light while transmitting red fluorescence light in the wavelength range of 590-750 nm or any subset of wavelengths in this range. When used in a fluorescence endoscopy video system with the light source filter 79A described above, the filter characteristics are such that any light outside of the wavelength range of 590-750 nm, or any desired subset of wavelengths in this range, contributes no more than 0.1% to the light transmitted by the filter.

The operation of an embodiment of the fluorescence endoscopy video system will now be described. The cameras 100A as shown in FIGS. 4A and 100B as shown in FIG. 4B or 100C as shown in FIG. 4C are capable of operating in color and fluorescence/reflectance imaging modes. A light source of the type shown in FIG. 2B, that provides a different output every video frame or field is required. In the color imaging mode, the processor/controller 64 provides a control signal to the multi-mode light source 52 that indicates the light source should be operating in the white light mode and provides a synchronizing signal. The light source 52 sequentially outputs filtered red, green, and blue light, synchronously with the video field or frame of the image sensors 102 and 104. The filtered light from the light source 52 is projected into the endoscope light guide 54 and is transmitted to the tip of the endoscope 60 to illuminate the tissue 58.

The processor/controller 64 also protects the sensitive low light image sensor 104 during color imaging by decreasing the gain of the amplification stage of the sensor. The light reflected by the tissue 58 is collected and transmitted by the endoscope image guide 56 to the camera where it is projected through beamsplitter 106 onto the monochrome image sensor 102, or the light is directly projected through the camera beamsplitter 106 onto the monochrome image sensor 102 if the sensor is located within the insertion portion of the endoscope. The image projected during each of red, green, and blue illuminations is transduced by the monochrome image sensor 102 and the resulting image signals are transmitted to the processor/controller 64.

Based on the brightness of the images captured, the processor/controller 64 provides a control signal to the multi-mode light source 52 to adjust the intensity control 80 and thereby adjust the level of light output by the endoscope light guide 54. The processor/controller 64 may also send a control signal to the camera 100A, 100B or 100C to adjust the gain of the monochrome image sensor 102.

The processor/controller 64 interpolates the images acquired during sequential periods of red, green, and blue illumination to create a complete color image during all time periods, and encodes that color image as video signals. The video signals are connected to color video monitor 66 for display of the color image. All of the imaging operations occur at analog video display rates (30 frames per second for NTSC format and 25 frames per second for PAL format).

When switching to the fluorescence/reflectance imaging mode, the processor/controller 64 provides a control signal to the multi-mode light source 52 to indicate that it should be operating in fluorescence/reflectance mode. In response to this signal, the light source filter wheel 79 stops rotating and the light source 52 selects and positions the appropriate blue optical filter 79A continuously into the optical path between the arc lamp 70 and the endoscope light guide 54. This change from sequentially changing filters to a static filter occurs in a period of approximately one second. Filter 79A transmits only those wavelengths of light that will induce the tissue 58 under examination to fluoresce. All other wavelengths of light are substantially blocked as described above. The filtered light is then projected into the endoscope light guide 54 and transmitted to the tip of the endoscope 60 to illuminate the tissue 58.

As part of setting the system in the fluorescence/reflectance mode, the processor/controller 64 also increases the gain of the amplification stage of the low light image sensor 104. The fluorescence emitted and excitation light reflected by the tissue 58 are either collected by the endoscope image guide 56 and projected through the camera beamsplitter 106 onto the low light image sensor 104 and the image sensor 102, or are collected and directly projected through the camera beamsplitter 106 onto the low light image sensor 104 and the image sensor 102 at the insertion tip of the endoscope 60. Spectral filter 118 limits the light transmitted to the low light image sensor 104 to either green or red autofluorescence light only and substantially blocks the light in the excitation wavelength band. The autofluorescence image is transduced by the low light image sensor 104. The reference reflected excitation light image is transduced by the monochrome image sensor 102 and the resulting image signals are transmitted to the processor/controller 64.

Based on the brightness of the transduced images, the processor/controller 64 may provide a control signal to the multi-mode light source 52 to adjust the intensity control 80 and thereby adjust the level of light delivered to the endoscope 60. The processor/controller 64 may also send control signals to the cameras 100A, 100B or 100C to adjust the gains of the low light image sensor 104 and the monochrome image sensor 102, in order to maintain constant image brightness while keeping the relative gain constant.

After being processed, the images from the two sensors are encoded as video signals by processor/controller 64. The fluorescence/reflectance image is displayed by applying the video signals to different color inputs on the color video monitor 66.

In order for the combined image to have optimal clinical meaning, for a given proportion of fluorescence to reference light signals emitted by the tissue and received by the system, a consistent proportion must also exist between the processed image signals that are displayed on the video monitor. This implies that the (light) signal response of the fluorescence endoscopy video system is calibrated. One suitable calibration technique is described in two patent applications previously incorporated herein by reference: U.S. patent application Ser. No. 09/615,965, and U.S. patent application Ser. No. 09/905,642.

The cameras 100A, 100B, 100C can be operated in a variation of the fluorescence/reflectance mode to simultaneously obtain fluorescence images and reflectance images with red, green, and blue illumination. The operation of the system is similar to that described previously for color imaging, so only the points of difference from the color imaging mode will be described.

In this variation of the fluorescence/reflectance mode, instead of changing from sequential red, green, and blue illumination to static blue illumination when switching from color imaging to fluorescence/reflectance imaging, the multi-mode light source 52 provides the same sequential illumination utilized in the color imaging mode, for all imaging modes. Capture and display of the light reflected by the tissue is similar to that described previously for the color imaging mode. However, in addition to the reflectance images captured in that mode, the gain of the amplification stage of the low light image sensor 104 is adjusted to a value that makes it possible to capture autofluorescence images during blue illumination. During red and green illumination, the gain of amplification stage of the low light sensor is decreased to protect the sensor while the image sensor 102 captures reflectance images.

In this modified fluorescence/reflectance mode, the camera captures both reflectance and fluorescence images during the blue illumination period, in addition to reflected light images during the red and green illumination periods. As for the color imaging mode, the reflectance images are interpolated and displayed on the corresponding red, green and blue channels of a color video monitor to produce a color image. Like the previously described fluorescence/reflectance mode, a fluorescence/reflectance image is produced by overlaying the fluorescence image and one or more of the reflectance images displayed in different colors on a color video monitor.

Since individual reflectance and fluorescence images are concurrently captured, both a color image and a fluorescence/reflectance image can be displayed simultaneously on the color video monitor. In this case, there is no need to utilize a separate color imaging mode. Alternatively, as described for the previous version of fluorescence/reflectance operation, only the fluorescence/reflectance image may be displayed during fluorescence/reflectance imaging and a color image displayed solely in the color imaging mode.

Yet another embodiment of this invention will now be described. All points of similarity with the first embodiment will be assumed understood and only points that differ will be described.

Figure 7A:
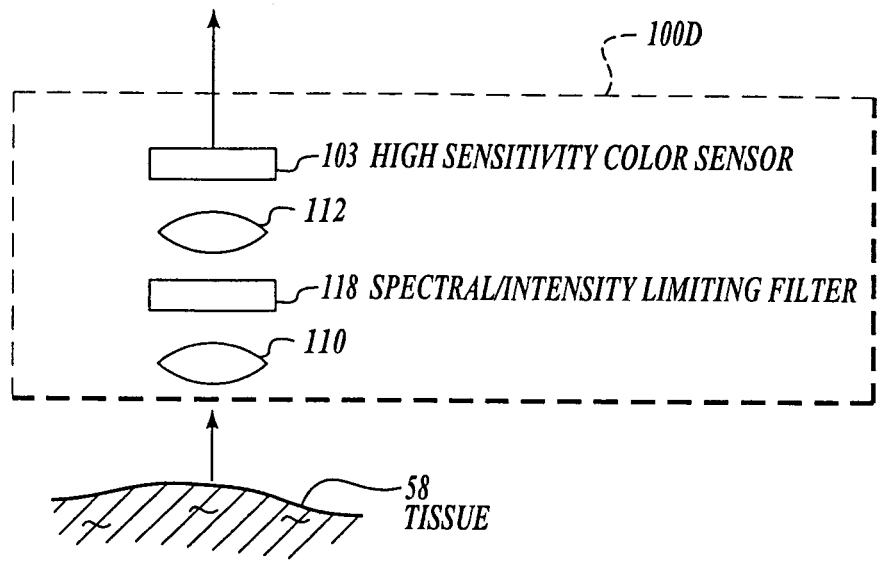
FIGS. 7A-7B illustrate additional embodiments of a camera according to the present invention that can acquire color, fluorescence/reflectance, and/or fluorescence/fluorescence images according to an embodiment of the present invention with optional placement for collimation and imaging optics.

In this second embodiment, all aspects of the fluorescence endoscopy video system are similar to those of the first embodiment except for the camera and the light source. A camera 100D for this embodiment of a system is as shown in FIG. 7A. It differs from the cameras 100A, 100B or 100C as described above in that all imaging modes utilize a single, low light color image sensor 103 (preferably a color CCD with charge carrier multiplication such as the Texas Instruments TC252) and that no beamsplitter is required. Alternatively, the color image sensor 103 may be a three-CCD with charge carrier multiplication color image sensor assembly, a color CCD, a three-CCD color image sensor assembly, a color CMOS image sensor, or a three-CMOS color image sensor assembly.

Each of the pixel elements on the low light color sensor 103 is covered by an integrated filter, typically red, green or blue (RGB). These filters define the wavelength bands of fluorescence and reflectance light that reach the individual pixel elements. Alternatively, the filter mosaic may be of the cyan, magenta, yellow, green (CMYG) variety. All mosaic filters typically have considerable overlap between their respective pass bands, which can lead to considerable crosstalk when imaging dim autofluorescence light in the presence of intense reflected excitation light. Therefore, a separate filter 118 is provided to reduce the intensity of reflected excitation light to the same level as that of the autofluorescence light and, at the same time, pass autofluorescence light. In addition, some conversion and image processing may be applied to convert CMYG filter responses to responses in RGB space. The signals from color image sensors with CMYG filter mosaics are converted to RGB signals by matrix conversions that are based on the specific layout of the CMYG mosaic pattern and the image sensor read-out architecture. Such conversions are routinely performed in color video systems and are taken to be understood by those of ordinary skill in the art.

In this embodiment, the primary fluorescence and reference images are projected onto the same image sensor 103, but, because of the individual filters placed over each pixel, these different images are detected by separate sensor pixels. As a result, individual primary fluorescence and reference image signals can be produced by processor/controller 64 from the single image sensor.

Figure 7B:
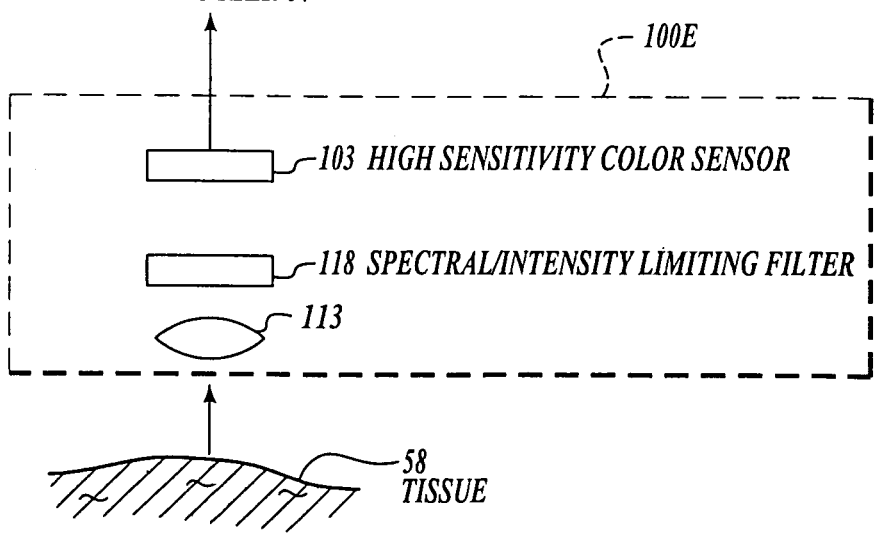

In FIG. 7A, light collimating optics 110 are positioned between the tissue 58 and filter 118 and imaging optics 112 are positioned immediately preceding the color image sensor 103. In an alternative optical configuration, camera 100E, as shown in FIG. 7B, eliminates the collimating optics 110 and imaging optics 112 and replaces them with a single imaging optics 113 located between the tissue 58 and filter 118. The advantage of this configuration is that all imaging is performed and controlled by the same imaging optics 113. The fact that filter 118 is located in a converging beam path must be considered in specifying that element and in the design of the imaging optics.

The operation of a system based on camera 100D of FIG. 7A or 100E of FIG. 7B will now be described. The cameras 100D and 100E are capable of operation in the color, fluorescence/fluorescence, and fluorescence/reflectance imaging modes. For a system based on camera 100D or 100E, a light source of the type shown in FIG. 2A, provides steady state output in each imaging mode. As described below, the light transmission specifications of the light source filters 76A, 76B, and 76C, the filter 118, and the mosaic color filters integrated with the image sensor 103 are selected such that the intensity of the reflected light and fluorescence light at the color image sensor's active elements results in transduced image signals with good signal-to-noise characteristics and without significant saturation. At the same time these filters have appropriate light transmission specifications for excitation and imaging of the primary fluorescence and for color imaging. The filter transmission characteristics are chosen to provide the desired ratio of relative primary fluorescence to reference light intensity at the image sensor.

In the color imaging mode, the processor/controller 64 provides a control signal to the multimode light source 52 that it should be in white light mode. The light source selects and positions the appropriate optical filter 76A into the optical path between the arc lamp 70 and endoscope light guide 54. Given the presence of filter 118 in cameras 100D, 100E which have reduced transmission for excitation light at blue wavelengths, the light source filter 76A should, in one embodiment, incorporate reduced transmission at red and green wavelengths or a slight peak in the blue (i.e., from 460-480 nm) to obtain a balanced color image at image sensor 103 with the proper proportions of red, green, and blue components.

Image signals from the color low light sensor 103 are processed by processor/controller 64. Standard techniques are utilized to produce a color image from a single color sensor. The image signals from pixels having the same filter characteristics are interpolated by processor/controller 64 to produce an image signal, related to the pass band of each element of the mosaic filter (e.g., red, green, and blue), at every pixel location. The resulting multiple images, which when combined produce a color image, are encoded by processor/controller 64 as video signals. The color image is displayed by connecting the video signals to the appropriate inputs of color video monitor 66.

Processor/controller 64 also maintains the overall image brightness at a set level by monitoring the brightness of the image signal at each pixel and adjusting the intensity of the light source output and camera amplifier gains according to a programmed algorithm.

When switching to the fluorescence/fluorescence imaging mode, processor/controller 64 provides a control signal to the multi-mode light source 52 to indicate that it should be in fluorescence/fluorescence mode. The light source 52 moves light source filter 76B into position in the light beam. Filter 76B transmits excitation light and blocks the transmission of light at the green and red fluorescence detection wavelengths, as described below. The characteristics of light source fluorescence excitation filter 76B and excitation filter 118, along with the mosaic filter elements on the color sensor 103, are such that the intensity of blue light at the color sensor is less than the intensities of red and green autofluorescence at the sensor, and are such that the ratio of the intensity of red autofluorescence to the intensity of green autofluorescence at the color sensor 103 has the appropriate value for optimal differentiation between normal and abnormal tissue. The fluorescence images are processed, as previously described for color imaging, by processor/controller 64 to produce separate images corresponding to each of the pass bands of the mosaic filter (e.g., RGB or CMYG). These separate images are encoded as video signals by processor/controller 64. A composite fluorescence/fluorescence image is displayed on the color video monitor 66 by applying the video signals from red and green image signals to different color inputs of the monitor. Alternatively, a composite image can be created in the image processor/controller 64 based on the relative intensities of the red and green image signals.

When switching to the fluorescence/reflectance imaging mode, processor/controller 64 provides a control signal to the multi-mode light source 52 to indicate that it should be in fluorescence/reflectance mode. The light source 52 moves light source filter 76C into position in the light beam. Filter 76C transmits both excitation light and reference light and blocks the transmission of light at fluorescence detection wavelengths, as described below. The characteristics of the light source filter 76C for fluorescence excitation and the reflectance illumination and the camera filter 118, along with the mosaic filter on the color sensor 103, as detailed below, are such that the intensity of reflected excitation light at the color sensor is comparable to the intensity of autofluorescence at the sensor, and should be such that the ratio of the intensity of autofluorescence to the intensity of reflected reference light at the color sensor 103 has the appropriate value. The fluorescence and reflectance images are processed, as previously described for color imaging, by processor/controller 64 to produce separate images corresponding to each of the pass bands of the mosaic filter (e.g., RGB or CMYG). These separate images are encoded as video signals by processor/controller 64. A composite fluorescence/reflectance image is displayed on color video monitor 66 by applying the video signals from the appropriate spectral bands (as discussed below) to different color inputs of the monitor or creating a composite image in the image processor/controller based on the relative intensities of the image signals received.

As indicated above, the filters in the light source and camera should be optimized for the imaging mode of the camera, the type of tissue to be examined and/or the type of precancerous tissue to be detected based on in vivo spectroscopy measurements. Although all of the filters described below can be made to order using standard, commercially available components, the appropriate wavelength range of transmission and degree of blocking outside of the desired transmission range for the described fluorescence endoscopy images modes are important to the proper operation of the system. The importance of other issues in the specification of such filters such as the fluorescence properties of the filter materials and the proper use of anti-reflection coatings are taken to be understood.

Filter characteristics for use in the fluorescence endoscopy video systems with a camera of the type shown in FIGS. 7A and 7B, operating in a fluorescence/reflectance imaging mode, or a fluorescence/fluorescence imaging mode, are shown in FIGS. 8A-8F. There are several possible configurations of fluorescence endoscopy video systems, operating in the fluorescence/reflectance imaging mode including green fluorescence with red reflectance, and red fluorescence with green reflectance and red or green fluorescence with blue reflectance. The particular configuration utilized depends on the target clinical organ and application. The filter characteristics will now be described for each of these four configurations.

Figures 8A, 8B, 8C, 8D, 8E, 8F:
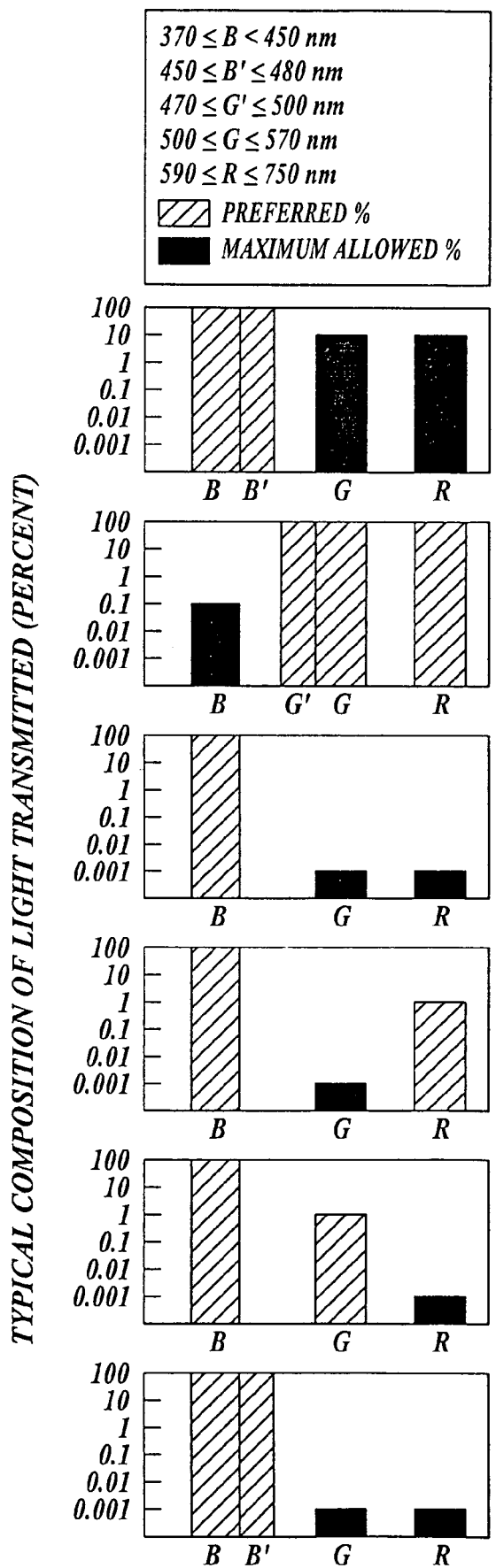
FIGS. 8A-8F are graphs illustrating transmission characteristics of filters for color imaging, fluorescence/fluorescence imaging, and fluorescence/reflectance imaging with the camera embodiment shown in FIGS. 7A-7B.

FIGS. 8A-8B illustrate one composition of the light transmitted by filters for a color imaging mode. FIG. 8A illustrates the composition of the light transmitted by the light source filter, such as filter 76A, which is used to produce light for color imaging. The spectral filter 118 remains in place during color imaging since there are no moving parts in the present camera embodiment. Accordingly, to achieve correct color rendition during color imaging it is necessary for the transmission of light source filter 76A to be modified, compared to the usual white light transmission for color imaging, such that the light received by the high sensitivity color sensor 103 is substantially white when a white reflectance standard is viewed with the camera. With a lamp having a flat output spectrum (e.g., a Xenon lamp), the transmission of filter 76A in the red and green spectral bands should be less than the transmission in the blue in order to balance the effect of spectral filter 118. In addition, the transmission of filter 76A in the blue extends to a long enough wavelength that there is an overlap with the short wavelength region of appreciable transmission of filter 118. Filter 76A transmits light in the blue wavelength range from 370-480 nm or any subset of wavelengths in this range at the maximum possible transmission. With a flat lamp spectrum the transmission of Filter 76A in the green and red wavelength range from 500-750 nm, or any subsets of wavelengths in this range, is preferably reduced by at least a factor of ten compared to the transmission in the blue, in order to achieve a balanced color image at the high sensitivity color sensor 103, after taking into account the effect of filter 118. As will be explained in further detail below, with a mercury lamp the output spectrum is less flat and a slightly different color correction is generally required in order to achieve a balanced color image at the image sensor.

FIG. 8B shows the composition of the light transmitted by the spectral filter 118, which is used for all imaging modes. In this configuration, the filter blocks the blue excitation light in the range 370-450 nm while transmitting red and green light in the wavelength range of 470-750 nm or any subsets of wavelengths in this range. When used in a fluorescence endoscopy video system in combination with the light source filter 76A described above, the filter characteristics are such that the intensity of light captured by high sensitivity color sensor 103 in the wavelength bands transmitted by the different regions of the sensor's mosaic filter are comparable, when a white reflectance standard is imaged. When used in a fluorescence endoscopy video system for fluorescence/fluorescence imaging in combination with the light source filter 76B described below, the filter characteristics are such that any light outside of the wavelength range of 470-750 nm (or any desired subset of wavelengths in this range) contributes no more than 0.1% to the light transmitted by the filter.

FIG. 8C illustrates the composition of the light transmitted by a filter, such as filter 76B, which is used to produce excitation light in the system light source. This filter transmits light in the wavelength range from 370-450 nm or any subset of wavelengths in this range. Of the light transmitted by this filter, preferably less than 0.001% is in the fluorescence imaging band from 470-750 nm (or whatever desired subsets of this range is within the transmission range of the primary and reference fluorescence wavelength bands defined by the transmission of the mosaic filter incorporated in the high sensitivity color sensor 103).

FIG. 8D illustrates the composition of the light transmitted by the light source filter, such as filter 76C, which is used to produce blue excitation light and red reference light for a green fluorescence and red reflectance imaging mode. This filter transmits light in the blue wavelength range from 370-450 nm, or any subset of wavelengths in this range. It also transmits light in the red wavelength range of 590-750 nm, or any subset of wavelengths in this range. The light transmitted in the red wavelength range (or subset of that range) is adjusted, as part of the system design, to be an appropriate fraction of the light transmitted in the blue wavelength range. This fraction is selected to meet the need to match the intensity of the reflected reference light projected on the color image sensor to the requirements of the sensor, at the same time as maintaining sufficient fluorescence excitation. Of the light transmitted by this filter, less than 0.001% is in the green wavelength range of 470-570 nm (or whatever desired subset of this range is specified as the transmission range of the primary fluorescence wavelength band).

FIG. 8E illustrates the composition of the light transmitted by a light source filter which is used to produce excitation light such as filter 76C described above for a red fluorescence and green reflectance imaging mode. This filter transmits light in the blue wavelength range from 370-450 nm or any subset of wavelengths in this range. It also transmits light in the green wavelength range of 470-570 nm or any subset of wavelengths in this range. The light transmitted in the green wavelength range (or subset of that range) is adjusted, as part of the system design, to be an appropriate fraction of the light transmitted in the blue wavelength range. This fraction is selected to meet the need to match the intensity of the reflected reference light projected on the color image sensor to the requirements of the sensor, at the same time as maintaining sufficient fluorescence excitation. Of the light transmitted by this filter, less than 0.001% is in the red fluorescence imaging wavelength range of 590-750 nm (or whatever desired subset of this range is specified as the transmission range of the primary fluorescence wavelength band).

FIG. 8F illustrates the composition of the light transmitted by a light source filter which is used to produce excitation light such as filter 76C described above for a red or green fluorescence and blue reflectance imaging mode. This filter transmits light in the blue wavelength range from 370-470 nm or any subset of wavelengths in this range. The light transmitted in the 450-470 nm wavelength range (or subset of that range) is adjusted, as part of the system design, to meet the need to match the intensity of the reflected reference light projected on the color image sensor to the requirements of the sensor and to provide the appropriate ratio of reference reflected light to fluorescence light, at the same time as maintaining sufficient fluorescence excitation. Of the light transmitted by this filter, less than 0.001% is in the fluorescence imaging wavelength range of 490-750 nm (or whatever desired subset of this range is specified as the transmission range of the primary fluorescence wavelength band).

A limitation of many fluorescence video endoscopy systems is that they typically employ the use of dedicated endoscopes. Fluorescence imaging with a dedicated fluorescence video endoscope is enabled by the use of an excitation barrier filter to block the strong excitation light used to excite the tissue fluorescence that these systems are intended to image. As described in the previous embodiments and shown in the corresponding figures, these barrier filters are built in to the endoscope distal end (typically between the objective lens and the low light image sensor) and this built-in filter distinguishes these endoscopes from those used for conventional videoendoscopy.

In an alternative embodiment of the present invention, fluorescence and color/white light images can be obtained by placing a barrier or blocking filter on the distal tip of a conventional video endoscope. The alternative embodiment of the present invention describes the use of an externally mounted filter in conjunction with a video endoscope that contains a sufficiently sensitive image sensor to image tissue fluorescence. This combination of a conventional video endoscope and an externally mounted barrier filter can be used in conjunction with an appropriate endoscopic light source and video processor/controller to image both in both color and fluorescence modes.

Figure 9:
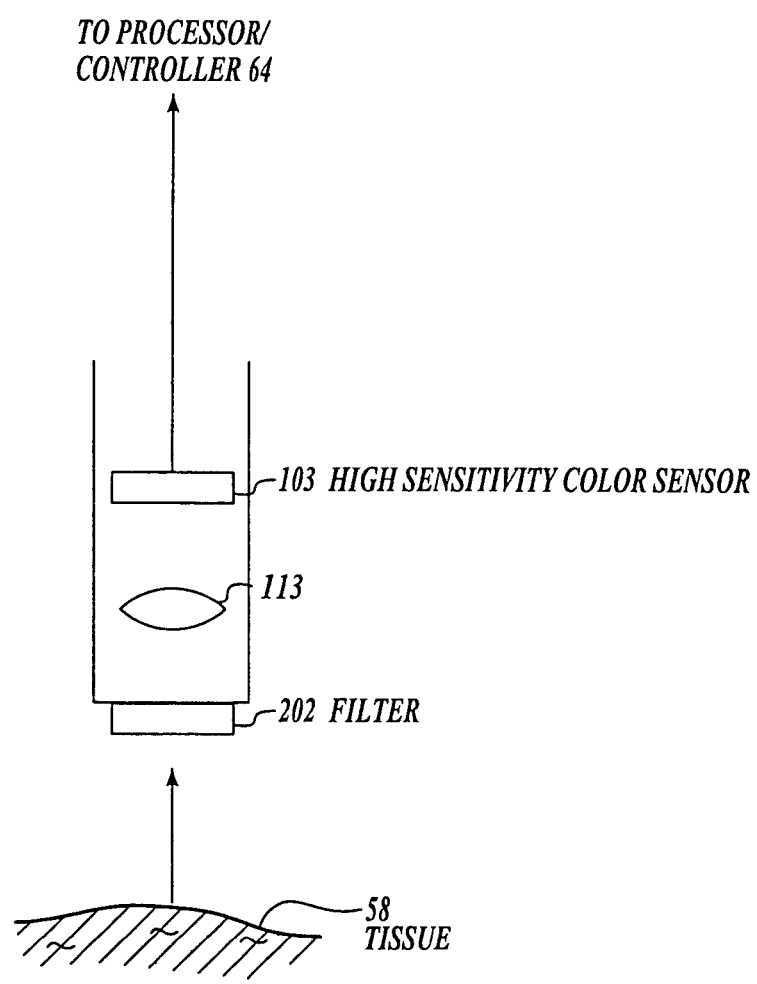
FIG. 9 illustrates a distal end filter in accordance with another embodiment of the present invention that allows a conventional endoscope to perform both fluorescence and white light imaging.

FIG. 9 illustrates one embodiment of a distal filter 202 that can be placed over the distal end of a conventional white light imaging endoscope to allow the endoscope to be used to perform fluorescence and white light examinations. As in previous embodiments and as will be described below, the filter 202 blocks excess excitation light from reaching the image sensor 103 but allows some blue light to pass in order to obtain white light images.

Figure 10:
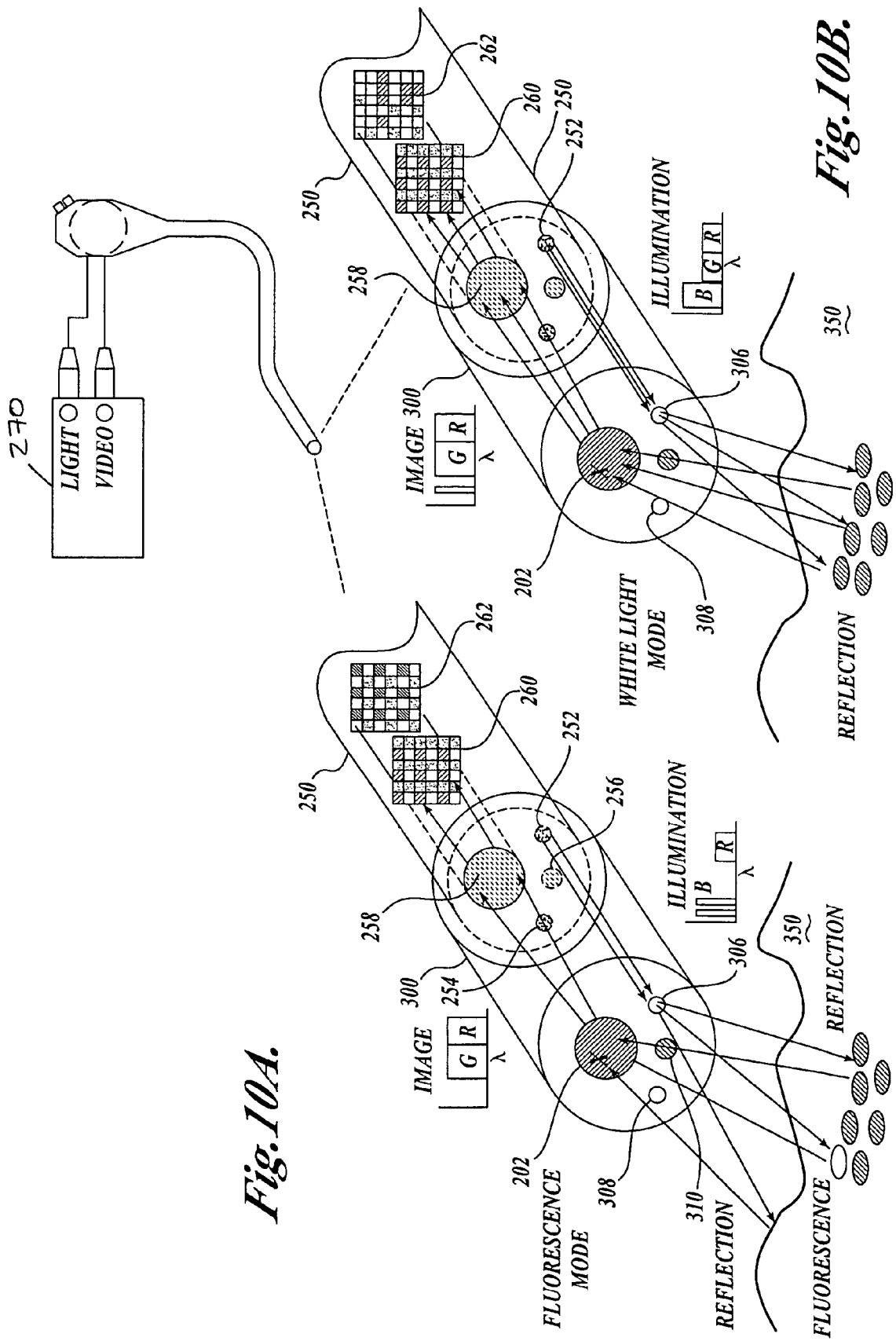
FIGS. 10A and 10B illustrate how the distal end filter allows the endoscope to perform fluorescence and white light imaging in accordance with one embodiment of the present invention.

FIGS. 10A and 10B illustrate the operation of the distal filter 202 in further detail. An endoscope 250 includes illumination ports 252, 254 that supply illumination light to an area of interest. A port 256 is the distal entrance to a working channel through which endoscopic tools can be passed in order to perform a desired task such as obtaining a biopsy sample, marking tissue with dye or perform some other diagnostic or therapeutic procedures. Light that is reflected from the tissue 350 is captured by a lens 258 that images the light onto a color image sensor 262. In this embodiment, the sensor includes a mosaic filter 260 that is positioned in front of a CCD, CMOS or equivalent image sensor 262. Image signals produced by the image sensor 262 are transmitted to a processor/controller (not shown) that converts the signals into video signals that are displayed on a video monitor. In addition the video signals may be recorded on a video tape, DVD or other storage media for later review or comparison.

In order to allow the endoscope to obtain both fluorescence and white light images of the tissue 350, the endoscope 250 may be fitted with the distal end filter 202. In the embodiment shown, the filter 202 is included in a filter assembly 300 that does not obscure the illumination ports 252, 254 in order to allow the illumination light to reach the tissue under examination. In addition the filter assembly 300 does not interfere with other distal tip features including but not limited to features such as water/air nozzles, electrodes, confocal imaging ports, or the working channel 256 so that tools can still be routed through the endoscope. The filter assembly is made of appropriately inert and non-conductive materials such as plastic or glass or stainless steel, so as also not to interfere with the particular material or electrical characteristics of the endoscope tip that may be required for use in conjunction with endotherapy techniques, such as argon ion plasma coagulation (APC), electrocautery, cryotherapy, or photodynamic therapy (PDT)

The filter 202 is positioned in front of the imaging lens 258 and prevents excitation light from reaching the image sensor. In one embodiment, the filter removes the excitation light having wavelengths in the range of 370-460 nm or some subset of this range but passes some blue light (e.g., >460 nm), and green and red light for use in white light imaging as described in previous embodiments and as will be in further described below. Because most endoscopes have objective lenses with a wide field of view, the filter should block excitation light over a corresponding wide field of view and over the range of angles of incidence of light collected by the endoscope objective. The filter should also be thin enough not to introduce optical aberrations or interfere with the mechanical properties and maneuverability of the endoscope tip. Dye-based absorption filters that block the desired range of excitation light and operate over a wide field of view may therefore be preferred for this application. Specific examples of such filters include Kodak Wratten gel filters or dyed polycarbonate or other optically clear plastic or glass materials. For durability, the filter is preferably constructed in a manner similar to optically protective eyewear such as laser goggles. As shown in FIG. 10A, the distal filter 202 allows fluorescence images to be obtained in at least two modes. In a first mode, excitation light, typically in the blue wavelength spectral band, is provided from a light source such as that described for previous embodiments and through the illumination ports 252, 254 whereupon it strikes the tissue 350. A portion of the excitation light is absorbed by the tissue and causes a tissue to produce fluorescence light while a portion of the excitation light is reflected by the tissue 350. Excitation light reflected by the tissue 350 is blocked by the filter 202 in the filter assembly 300, while the tissue fluorescence light and light in other spectral bands passes through the filter 202.

In one fluorescence imaging mode, only fluorescence light is used to produce video images of the tissue. In another mode, the tissue is illuminated with the excitation light and some amount of reflectance light. As shown in FIG. 10A, the reflectance light is in the red spectral band. The reflectance light passes through the filter 202 and the filter 260 in front of the image sensor 262. Images of the tissue are obtained by combining for example, the green image signals from the image sensor 262 to obtain a fluorescence image in the green spectral band and the red image signals from the image sensor 262 to obtain a reflectance image in the red spectral band. Alternatively, the reflectance light may be provided in the green spectral band and a red fluorescence image obtained. In yet another embodiment, blue reflectance light having wavelengths that are not filtered by the filter 202 can be used to produce the reflectance image. The fluorescence and reflectance images may be combined for display for a viewer. As in previous embodiments in order to prevent the reflectance image from overpowering the fluorescence image, the amount of reflectance light supplied from the light source is selected to be comparable to the amount of fluorescence light received by the image sensor 262.

As shown in FIG. 10B, the endoscope 250 can also be used to obtain white light images of the tissue 350 by illuminating the tissue with light including red, green and blue spectral components. The illumination light is reflected by the tissue sample 350, passes through the filter 202 and is focused onto the mosaic filter 260 of the color image sensor 262 by the endoscope's imaging lens 258. Because the filter 202 removes most of the blue reflectance light, the light received by the image sensor 262 may include proportionally more red and green light. To compensate for the reduced blue light at the image sensor, the illumination light should either contain additional blue light in the band that passes through the filter 202 or proportionally less green and red light so that the resulting image produced from the image sensor signals may be white balanced. Additional fine tuning of the white balance of the images produced by the image sensor 262 can be accomplished by image processing software in the processor/controller (not shown).

Figure 11:
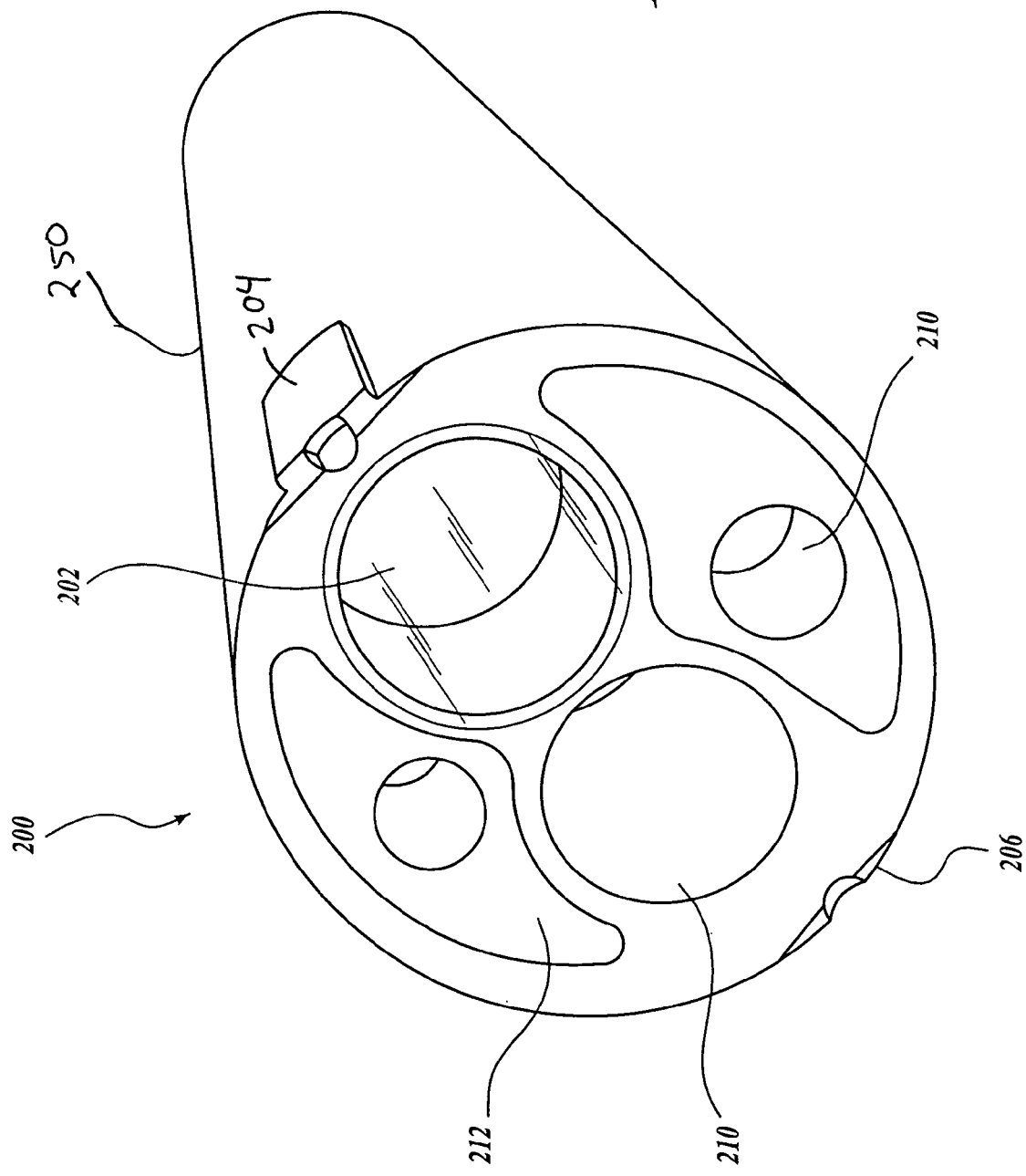
FIG. 11 illustrates one embodiment of a distal end filter that can be secured to a conventional endoscope in accordance with the present invention.

One embodiment of a filter assembly 200 that is placed on the distal tip of an endoscope is shown in FIG. 11. A filter 202 may be mounted in a frame that is snap-fitted over the distal end face of an endoscope. The filter and/or frame are secured to the endoscope with a mechanical, adhesive, magnetic force or other means. In one embodiment, the frame includes a set of proximally extending tabs 204, 206 that are secured to the outer circumference of the endoscope tip.

The filter 202 is positioned in front of the imaging lens of the endoscope. As indicated above, the filter 202 operates to remove a substantial portion of reflected blue excitation light used during the fluorescence imaging mode. In the embodiment shown in FIG. 11, the frame also includes a hole 210 that is positioned over the working channel of the endoscope in order to allow tools, such as biopsy forceps, snares, cytology brushes, etc., to be passed through the working channel. Positioned on either side of the frame are holes 212, 214 that allow light from the illumination guides to pass through the frame.

FIG. 12 shows further detail of a filter 202 secured in front of an imaging lens 258 in order to allow a conventional endoscope to perform both white light and fluorescence imaging. In this embodiment, the filter 202 is formed from a dyed polycarbonate extruded film and bonded to the lens 258 with an optically clear adhesive.

In one embodiment, the filter 202 is a 65 µm thick optical grade polycarbonate film dyed with solvent yellow 33 at a concentration of 0.8% by weight. The film is secured to the lens of the endoscope with a 50 µm thick layer of an optical adhesive. Other dyes, thicknesses and/or concentrations could be used, depending on the spectral characteristics of the light source used to provide the illumination and excitation light, the response of the imager and the particular fluorescence bands to be viewed.

The extruded film can be die cut and packaged as a kit with an amount of adhesive to allow owners of white light imaging endoscopes to convert their endoscopes into devices that perform both white light imaging and fluorescence imaging when used with a light source that generates excitation light for fluorescence imaging and a color corrected illumination light that compensates for the presence of the filter 202.

Figure 13A:
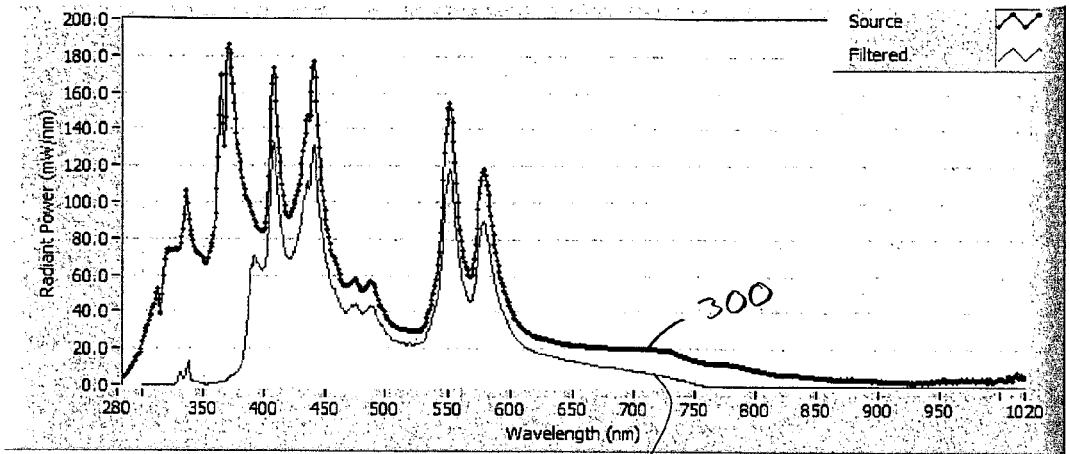
FIGS. 13A-13E are spectral graphs showing the operation of filters in the light source and in front of an image sensor in accordance with an embodiment of the present invention.

FIGS. 13A-13E are spectral graphs showing the spectra of light produced by a light source, a distal blocking filter and a color correction filter in accordance with an embodiment of the present invention. In the example shown, the light source contains an Osram HXP R 200W/45 arc lamp described above. FIG. 13A shows a spectrum 300 of the intensity of the light produced by the unfiltered arc lamp. As can be seen the light has significant peaks at in the blue range below 450 nanometers as well as in the green/yellow range from 540-580 nanometers. A spectrum 302 shows the result when light from the arc lamp is filtered by a conventional ultraviolet (UV) and infrared (IR) filter.

Figure 13B:
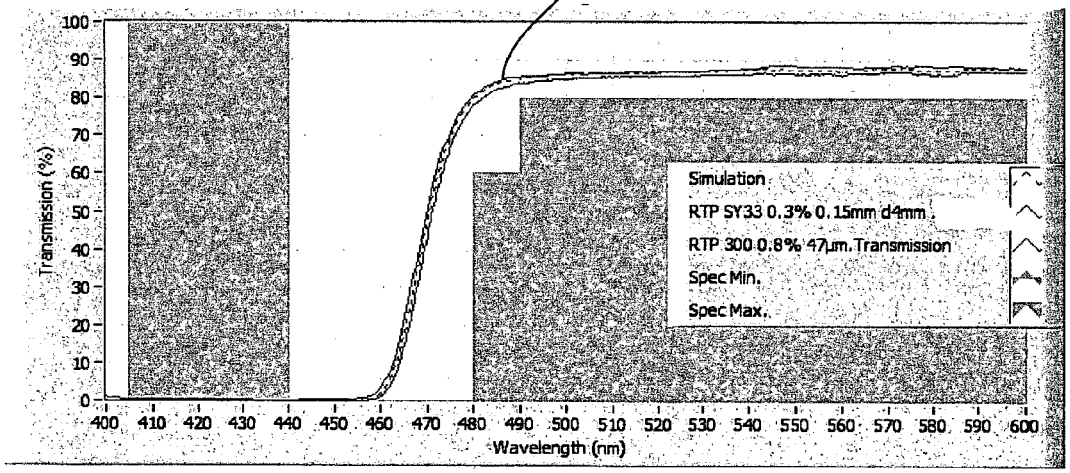

FIG. 13B illustrates the passband characteristics 304 of the filter 202 positioned at the distal end of the endoscope. In the example shown, the filter made of a 65 µm thick optical grade polycarbonate film dyed with solvent yellow 33 at a concentration of 0.8% by weight. As can be seen, the filter 202 blocks light having wavelengths below 460 nanometers and passes light having wavelengths above 460 nanometers.

Figure 13C:
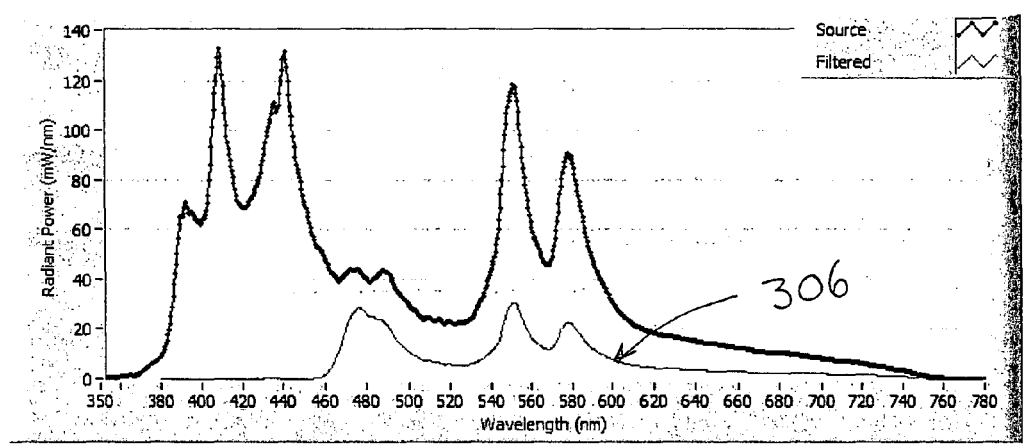

The spectra of the light when filtered by the UV, IR and distal blocking filter 202 are shown in FIG. 13C. The light contains a spike of blue light at about 480 nanometers that is used for to produce the blue component of a white light image. However, the light also contains spikes of green and yellow wavelengths at approximately 550 and 580 nanometers. In order to produce color balanced white light images, the amounts of blue, green and red light reaching the image sensor should be approximately the same. Therefore a color correction filter may be placed to filter the light from the light source during white light imaging.

Figure 13D:
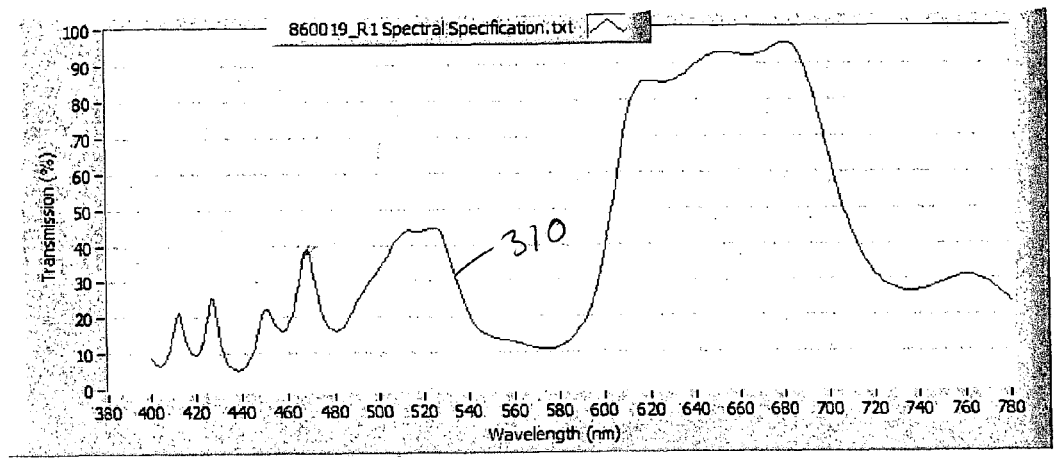

FIG. 13D shows the passband characteristics 310 of one suitable color correction filter. The color correction filter passes the blue light at approximately 470 nanometers but suppresses the green/yellow light from 540-580 nanometers so that the levels of red, green and blue light reaching the image sensor allow the creation of white balanced color images of the tissue. Suitable color correction filters can be obtained commercially from Barr Associates, Inc. of Westford, Mass. As will be appreciated the particular characteristics required of the color correction filter may depend on such factors as the spectral characteristics of the light source, the optics of the endoscope, the image sensor within the endoscope etc. Therefore the filters and light source described are merely exemplary and not limiting of the present invention.

Figure 13E:
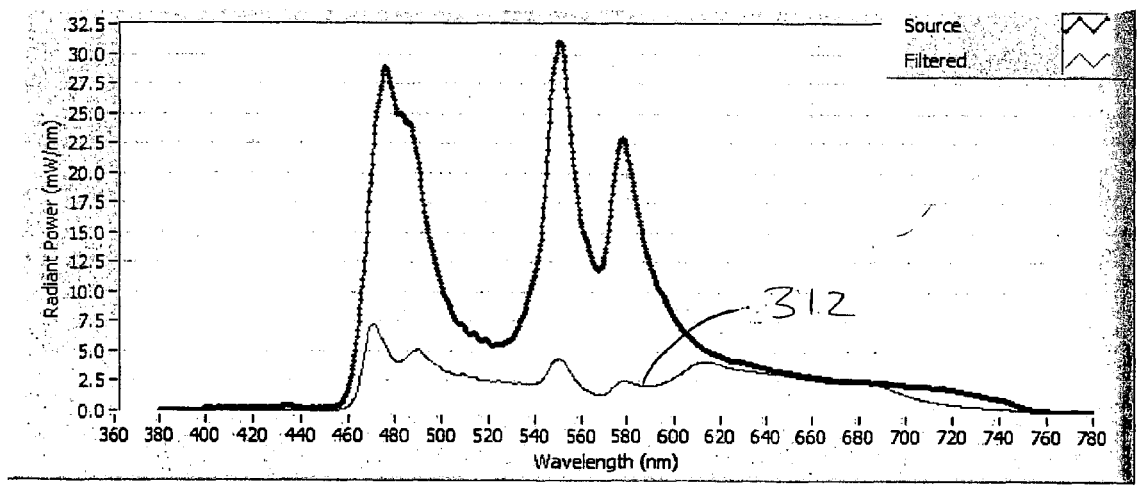

The spectra 312 of the illumination light when filtered by the UV, IR blocking filter and color correction filter are shown in FIG. 13E. As can be seen, the spectra contains reduced green and yellow components in order to produce color balanced white light images.

Another embodiment of the present invention also utilizes a filter on the distal tip of a video endoscope. Some video endoscope systems do not employ the use of color image sensors and instead use sequential illumination in various spectral (e.g., blue, green, red) bands and then combine monochrome images to produce full color images. An external barrier filter 202 can be used in an endoscope of the type shown in FIG. 9 with the high sensitivity color sensor 103 replaced by a monochrome image sensor and sequential illumination of the type discussed in connection with FIG. 2B.

Briefly, in accordance with one embodiment of the invention, autofluorescence images are obtained by illuminating with an excitation light. Color images are obtained by sequential illumination with red, green and blue light; wherein the blue light either includes wavelengths or is limited to wavelengths not blocked by the filter 202.

The fluorescence endoscopy video systems described in the above embodiments have been optimized for imaging endogenous tissue fluorescence. They are not limited to this application, however, and may also be used for photo-dynamic diagnosis (PDD) applications. As mentioned above, PDD applications utilize photo-active drugs that preferentially accumulate in tissues suspicious for early cancer. Since effective versions of such drugs are currently in development stages, this invention does not specify the filter characteristics that are optimized for such drugs. With the appropriate light source and camera filter combinations, however, a fluorescence endoscopy video system operating in either fluorescence/fluorescence or fluorescence/reflectance imaging mode as described herein may be used to image the fluorescence from such drugs.

As will be appreciated, each of the embodiments of a camera for a fluorescence endoscopy video system described above, due to their simplicity, naturally lend themselves to miniaturization and implementation in a fluorescence video endoscope, with the camera being incorporated into the insertion portion of the endoscope. The cameras can be utilized for both color imaging and fluorescence imaging, and in their most compact form contain no moving parts.

The invention claimed is:

1. A filter assembly for use with an imaging endoscope, comprising:
a filter configured to be coupled externally with a distal end of the imaging endoscope, the filter being made of a dye-impregnated film, the filter being positioned between an imaging lens and a tissue to be imaged, the filter being configured to block excitation light from reaching an image sensor of the endoscope, such that the image-sensor produces fluorescence images, the filter also being configured to pass an amount of blue light such that the image sensor produces white light images of the tissue.

2. The filter assembly of claim 1, wherein the filter blocks excitation light having wavelengths in a range of 370-460 nm.

3. The filter assembly of claim 1, wherein the filter passes light having wavelengths greater than 460 nm.

4. The filter assembly of claim 1, further comprising means for securing the filter to the distal end of the endoscope.

5. The filter assembly of claim 4, wherein the means for securing the filter includes one or more tabs that are secured to the distal end of the endoscope.

6. The filter assembly of claim 4, wherein the means for securing the filter includes a magnet.

7. The filter assembly of claim 4, wherein the means for securing the filter includes a sleeve that fits over the distal end of the endoscope.

8. The filter of claim 1, wherein the dye-impregnated film is a polycarbonate film.

9. The filter of claim 1, wherein the filter is bonded to the imaging lens of the endoscope with an optically clear adhesive.

10. The filter of claim 8, wherein the dye is solvent yellow 33.

11. The filter of claim 10, wherein the dye has a concentration of 0.8%.

12. The filter of claim 11, wherein the filter passes light having wavelengths greater than 460 nm.

13. An endoscope assembly, comprising:
a white-light imaging endoscope; and
a filter configured to be coupled externally with a distal end of the imaging endoscope, the filter being made of a dye-impregnated film, the filter being positioned external to the endoscope in front of between an imaging lens at a distal end of the endoscope and a tissue to be imaged, the filter being configured to block excitation light from reaching an image sensor of the endoscope, such that the image-sensor produces fluorescence images, the filter also being configured to pass an amount of blue light such that the image sensor produces white light images of the tissue.

14. The assembly of claim 13, wherein the filter blocks excitation light having wavelengths in a range of 370-460 nm.

15. The assembly of claim 13, wherein the filter passes light having wavelengths greater than 460 nm.

16. The assembly of claim 13, wherein the white-light imaging endoscope includes at least one illumination port, said filter assembly being configured such that it does not interfere with said at least one illumination port.

17. The assembly of claim 13, further comprising means for securing the filter to the distal end of the endoscope.

18. The assembly of claim 13, wherein the dye-impregnated film is a polycarbonate film.

19. The assembly of claim 18, wherein the dye is solvent yellow 33 and has a concentration of 0.8%.

20. The assembly of claim 13, wherein the filter is bonded to the imaging lens of the endoscope with an optically clear adhesive.

* * * * *